United States Patent [19]

Natsugari et al.

[11] Patent Number: 5,523,305
[45] Date of Patent: Jun. 4, 1996

[54] TACHYKININ RECEPTOR ANTAGONISTS, ISOQUINOLONES AND THEIR PRODUCTION

[75] Inventors: Hideaki Natsugari, Ashiya; Hideo Shirafuji, Nagaokakyo; Takayuki Doi, Izumi, all of Japan

[73] Assignee: Takeda Chemical Industries, Ltd., Osaka, Japan

[21] Appl. No.: 45,219

[22] Filed: Apr. 13, 1993

[30] Foreign Application Priority Data

Apr. 15, 1992 [JP] Japan .................. 4-095291

[51] Int. Cl.⁶ .................. C07D 215/38; A61K 31/47
[52] U.S. Cl. .................. 514/309; 546/141
[58] Field of Search .................. 546/141; 514/309

[56] References Cited

U.S. PATENT DOCUMENTS

| | | | |
|---|---|---|---|
| 2,647,902 | 8/1953 | Aschner | 546/141 |
| 2,809,969 | 10/1957 | Speeter | 546/141 |
| 3,247,212 | 4/1966 | Johnson | 546/141 |
| 3,600,394 | 8/1971 | Coyne | 546/141 |
| 3,980,655 | 9/1976 | Kunstmann | 546/141 |

FOREIGN PATENT DOCUMENTS

| | | |
|---|---|---|
| 0421456 | 1/1990 | European Pat. Off. . |
| 0472116 | 8/1991 | European Pat. Off. . |
| 0481243 | 9/1991 | European Pat. Off. . |
| 0481383 | 10/1991 | European Pat. Off. . |
| WO9109017 | 12/1990 | WIPO . |

*Primary Examiner*—Gary Geist
*Assistant Examiner*—Catherine Kilby Scalzo
*Attorney, Agent, or Firm*—Foley & Lardner

[57] ABSTRACT

Novel composition represented by the formula:

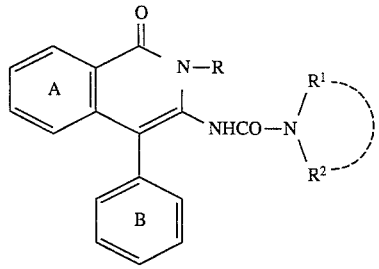

wherein ring A and ring B each means a benzene ring which may be substituted; R means a hydrogen atom or an alkyl group which may be substituted; $R^1$ means a hydrogen atom or an alkyl group which may be substituted; $R^2$ means a hydrocarbon group which may be substituted or a heterocyclic group which may be substituted, or $R^1$ and $R^2$, taken together with the adjacent nitrogen atom, jointly form a ring which may be substituted, or a pharmaceutically acceptable salt thereof which is a useful tachykinin receptor antagonist.

17 Claims, No Drawings

TACHYKININ RECEPTOR ANTAGONISTS, ISOQUINOLONES AND THEIR PRODUCTION

The present invention relates to a tachykinin receptor antagonist composition, a heterocyclic compound having such antagonist activity and a method for the production thereof.

As compounds having substance P receptor antagonizing activity, the following are known.

(1) in EP-A-333,174 a compound of the formula:

wherein $R^1$ is hydrogen or an amino-protecting group; $R^2$ is hydrogen, an amino-protecting group, a carbamoyl(lower)alkyl group, a carboxy(lower)alkyl group or a protected carboxy(lower)alkyl group; $R^3$ is an ar(lower)alkyl group, a group of the formula:

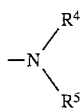

wherein $R^4$ and $R^5$ are each hydrogen, aryl or lower alkyl which may have suitable substituent(s), or $R^4$ and $R^5$ are linked together to form benzene-condensed lower alkylene or a group of the formula:

wherein $R^6$ is hydrogen, aryl or lower alkyl which may have suitable substituent(s); A is a single bond or one or two amino acids residue, provided when A is one amino acid residue of -D-Trp-, then $R^4$ is not hydrogen; and a salt thereof, (2) in EP-A-436,334 among others, a compound of the formula:

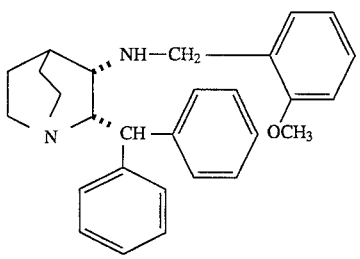

(3) in EP-A-429,366 among others, a compound of the formula:

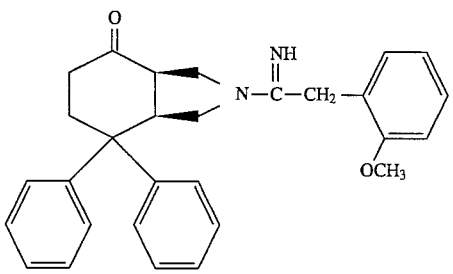

(4) in Journal of Medicinal Chemistry, 34, p1751, 1991 among others, a compound of the formula:

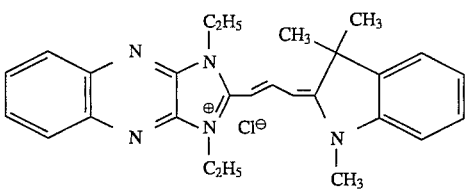

In addition, the heterocyclic compounds [A] indicated below in Table 1 are also known. However, there is no disclosure ever suggesting that these compounds have any activity related to substance P receptor.

[TABLE 1]

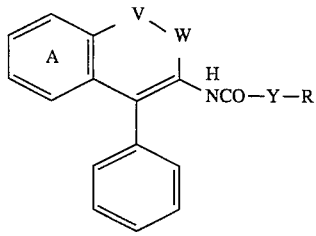

| Corresponding patent application | V | W | —Y—R | Use |
|---|---|---|---|---|
| US 3862152 | —N= | =CH— | H<br>—N—$R^3$<br>($R^3$ = alkyl, aryl, aralkyl, etc.) | Anti-ulcer agent |
| EP 354994 | (O)$_m$<br>↑<br>—N= | =CH— | H<br>—N—(CH$_2$)$_n$—⌬<br>etc. | ACAT inhibitor |

[TABLE 1]-continued

| Corresponding patent application | V | W | −Y−R | Use |
|---|---|---|---|---|
| EP 421456 | R¹<br>\|<br>−N−, −N= | R²<br>\|<br>−CO−, =C− | H<br>\|<br>−N−(CH₂)ₙ— phenyl<br>etc. | ACAT inhibitor |

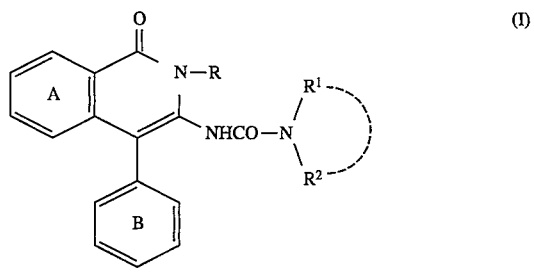

Tachykinin is a generic term denoting a group of neuropeptides. In mammalian animals, substance P, neurokinin-A and neurokinin-B are known. It is also known that by binding their respective receptors (neurokinin-1, neurokinin-2, neurokinin-3) present in the living body, these peptides exhibit a diversity of biological activities.

Among them, substance P is a neuropeptide known for the longest time of all and studied in the greatest detail. Substance P is known to play a critical role as a transmitter substance in both the peripheral and central nervous systems. This substance is also suspected to be involved in a variety of morbid states (pain, inflammation, allergy, mental disease, etc.). Such being the case, for use as drugs for the treatment of the above-mentioned disease states, the development of compounds having potent tachykinin receptor antagonizing activity, particularly high antagonistic activity against substance P receptor, as well as other favorable properties such as safety and a sufficiently long duration of action after administration has been looked after in earnest.

The object of the present invention is to provide a medicinally useful tachykinin receptor antagonist composition or preparation comprising a heterocyclic compound or salt distinguished structurally from any of the known compounds mentioned above and having improved tachykinin receptor antagonizing activity, novel heterocyclic compounds having such antagonistic activity, and a commercially useful method for the production thereof.

The inventors of the present invention, taking note of the above circumstances, did much research and ultimately found that a compound or its salt having the following skeletal structure has a surprisingly high tachykinin receptor antagonizing activity, particularly high antagonistic activity against substance P receptor. They accordingly perfected the present invention.

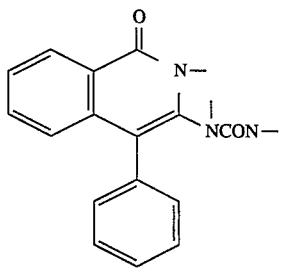

The present invention, as such, is directed to (1) a tachykinin receptor antagonist composition comprising a compound of the formula:

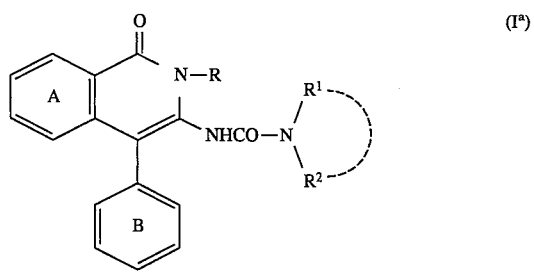

(I)

wherein ring A and ring B each means a benzene ring which may be substituted; R means a hydrogen atom or an alkyl group which may be substituted; R¹ means a hydrogen atom or an alkyl group which may be substituted; R² means a hydrocarbon group which may be substituted or a heterocyclic group which may be substituted, or R¹ and R², taken together with the adjacent nitrogen atom, jointly form a ring which may be substituted; or a salt thereof, (2) a novel compound of the formula:

(Iᵃ)

wherein ring A and ring B each means a benzene ring which may be substituted; R means a hydrogen atom or an alkyl group which may be substituted; R¹ means a hydrogen atom or an alkyl group which may be substituted; R² means a hydrocarbon group which may be substituted or a heterocyclic group which may be substituted, or R¹ and R², taken together with the adjacent nitrogen atom, jointly form a ring which may be substituted, with the proviso that when R¹ is a hydrogen and R² is a phenyl substituted with alkyl or halogen, ring A is substituted with two alkyl groups or two halogens and ring B is unsubstituted or substituted with a halogen, or a salt thereof.

(3) a process for producing the compound (Iᵃ) or a salt thereof which comprises reacting a compound of the formula:

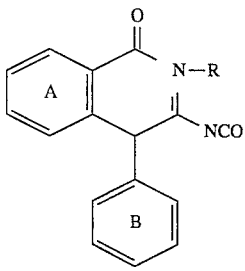

(II)

wherein each symbol has the same meaning as defined hereinabove or a salt thereof with a compound of the formula:

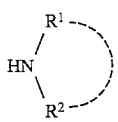

(III)

wherein each symbol has the same meaning as defined hereinabove or a salt thereof; and (4) a process for producing the compound (Iᵃ) or a salt thereof which comprises reacting a compound of the formula:

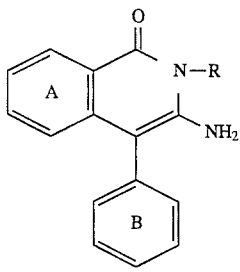

(IV)

wherein each symbol has the same meaning as defined hereinabove or a salt thereof with a compound of the formula:

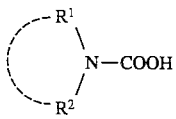

(V)

wherein each symbol has the same meaning as defined hereinabove or a salt or reactive derivative thereof.

Referring to the above formulas, ring A and ring B each is a benzene ring which may be substituted. The substituent or substituents that may be present on this benzene ring include, among others, halogen atoms, alkyl groups which may be halogenated, alkoxy groups which may be halogenated, alkylthio groups which may be halogenated, $C_{1-7}$ acylamino groups (e.g. formylamino, acetylamino, propionylamino, butyrylamino, benzoylamino, etc.), $C_{1-3}$ acyloxy groups (e.g. formyloxy, acetoxy, propionyloxy, etc.), hydroxyl, nitro, cyano, amino, mono- or di-$C_{1-4}$ alkylamino groups (e.g. methylamino, ethylamino, propylamino, dimethylamino, diethylamino, etc.), cyclic amino groups (e.g., 5- to 9-membered cyclic amino which may contain 1 to 3 hetero-atoms such as oxygen and sulfur in addition to nitrogen as ring-constituent members, such as pyrrolidino, piperidino, morpholino, etc.), $C_{1-4}$ alkyl-carbonylamino groups (e.g. acetylamino, propionylamino, butyrylamino, etc.), $C_{1-4}$ alkylsulfonylamino groups (e.g. methylsulfonylamino, ethylsulfonylamino, etc.), $C_{1-4}$ alkoxy-carbonyl groups (e.g. methoxycarbonyl, ethoxycarbonyl, propoxycarbonyl, etc.), carboxyl, $C_{1-6}$ alkyl-carbonyl groups (e.g. methylcarbonyl, ethylcarbonyl, propylcarbonyl, etc.), carbamoyl, mono- or di-$C_{1-4}$ alkylcarbamoyl groups (e.g. methylcarbamoyl, ethylcarbamoyl, etc.) and $C_{1-6}$ alkylsulfonyl groups (e.g. methylsulfonyl, ethylsulfonyl, propylsulfonyl, etc.).

As the halogen atoms, among the above-mentioned substituents, fluoro, chloro, bromo and iodo may be reckoned and chloro or fluoro is preferred.

As the alkyl groups which may be halogenated, there may be mentioned straight-chain or branched $C_{1-6}$ alkyl groups which may be substituted by 1 to 5 halogen atoms such as those mentioned above and specifically methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl, 5-trifluoromethylpentyl, etc. can be exemplified. Preferred are straight-chain or branched $C_{1-4}$ alkyl groups which may be substituted by 1 to 3 halogen atoms such as those mentioned above, such as methyl, chloromethyl, difluoromethyl, trichloromethyl, trifluoromethyl, ethyl, 2-bromoethyl, 2,2,2-trifluoromethylethyl, propyl, 3,3,3-trifluoropropyl, isopropyl, 2-trifluoromethylethyl, butyl, 4,4,4-trifluorobutyl, isobutyl, sec-butyl, tert-butyl and so on.

As said alkoxy groups which may be halogenated or said alkylthio groups which may be halogenated, there can be mentioned optionally halogenated alkoxy or alkylthio groups which are formed by bonding an oxygen atom or sulfur atom and respectively the alkyl or halogenated alkyl group which are mentioned above.

As said alkoxy groups which may be halogenated, there can be mentioned straight-chain or branched $C_{1-6}$ alkoxy groups which may be substituted by 1 to 5 halogen atoms such as those mentioned hereinbefore, such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy, etc. Preferred are straight-chain or branched $C_{1-4}$ alkoxy groups and those alkoxy groups substituted by 1 to 3 halogen atoms such as those mentioned hereinbefore, such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.

As said alkylthio groups which may be halogenated, there can be mentioned straight-chain or branched $C_{1-6}$ alkylthio groups which may be substituted by 1 to 5 halogen atoms such as those mentioned hereinbefore, such as methylthio, difluoromethylthio, trifluoromethylthio, ethylthio, propylthio, isopropylthio, butylthio, 4,4,4-trifluorobutylthio, pentylthio, hexylthio and so on. Preferred are straight-chain or branched $C_{1-4}$ alkylthio groups and those alkylthio groups substituted by 1 to 3 halogen atoms such as those mentioned hereinbefore, such as methylthio, difluoromethylthio, trifluoromethylthio, ethylthio, propylthio, isopropylthio, butylthio, 4,4,4-trifluorobutylthio, etc.

The substituent groups on ring A or ring B may be present in optional positions of the ring and, where two or more substituents are present, they may be the same or different. The number of substituents may range from 1 to 4. The adjacent carbon atoms on ring A or ring B may be bound to —$(CH_2)_n$— (n means an integer of 3 to 5) to form a 5- to 7-membered ring such as cyclopentene, cyclohexene, cycloheptene, etc. and the compounds formed in this manner are also included in the objective compound (I).

Referring to ring A, concrete examples of the

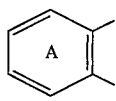

include groups of the formula:

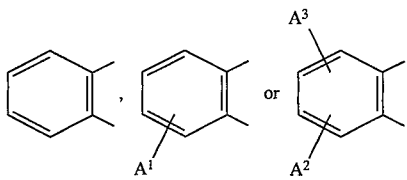

where $A^1$, $A^2$ and $A^3$ are the same or different and each means a halogen atom such as chloro, fluoro, etc., a $C_{1-4}$ alkyl group such as methyl, ethyl, isopropyl, etc., or a $C_{1-4}$ alkoxy group such as methoxy etc.

Preferred examples of ring A are groups of the formula:

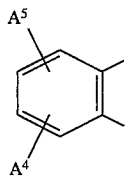

wherein $A^4$ and $A^5$ are the same or different and each means a $C_{1-4}$ alkyl group such as methyl, etc. Particularly preferred examples are groups of the formula:

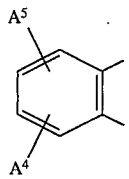

wherein $A^4$ and $A^5$ are as defined above.

Referring to ring B, concrete examples of the

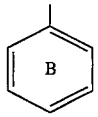

include groups of the formula:

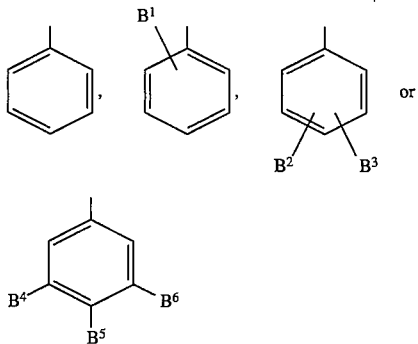

where $B^1$, $B^2$, $B^3$, $B^4$, $B^5$ and $B^6$ are the same or different and each means a halogen atom such as chloro, fluoro, etc., a $C_{1-4}$ alkyl group such as methyl, ethyl, etc., or a $C_{1-4}$ alkoxy group such as methoxy, etc.

Preferred examples of the ring B are groups of the formula:

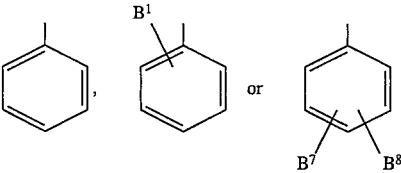

wherein $B^1$ is the same meaning hereinbefore, and $B^7$ and $B^8$ are the same or different and each means a halogen atom such as fluoro, etc., or a $C_{1-4}$ alkyl group such as methyl, etc. Particularly preferred examples are groups of the formula:

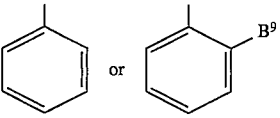

wherein $B^9$ is a $C_{1-4}$ alkyl group such as methyl, etc.

Referring to the above formulas, R means a hydrogen atom or an alkyl group which may be substituted. The "alkyl group" of the "alkyl group which may be substituted", which is represented by R, is a straight-chain or branched $C_{1-6}$ alkyl group, a $C_{3-6}$ cycloalkyl group or a $C_{3-6}$ cycloalkyl-$C_{1-4}$ alkyl group, for instance. The straight-chain or branched $C_{1-6}$ alkyl group mentioned above includes methyl, ethyl, propyl, isopropyl, butyl, isobutyl, sec-butyl, tert-butyl, pentyl, neopentyl, hexyl and so on. Preferred are straight-chain or branched $C_{1-4}$ alkyl groups such as methyl, ethyl, propyl, isopropyl, butyl, isobutyl, sec-butyl, tert-butyl and so on. The $C_{3-6}$ cycloalkyl group may for example be cyclopropyl, cyclopentyl or cyclohexyl. The $C_{3-6}$ cycloalkyl-$C_{1-4}$ alkyl group includes, among others, cyclopropylmethyl and cyclopropylethyl.

The substituent group(s) optionally substituting said alkyl group include halogen atoms (e.g. fluoro, chloro, bromo, iodo, etc.), nitro, cyano, hydroxyl, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio etc.), amino, mono- or di-$C_{1-4}$ alkylamino groups (e.g. methylamino, ethylamino, propylamino, dimethylamino, diethylamino, etc.), cyclic amino groups (e.g. 5- to 9-membered cyclic amino groups which may contain 1 to 3 hetero-atoms such as oxygen and sulfur in addition to nitrogen as ring-constituent members, such as pyrrolidino, piperidino, morpholino, etc.), $C_{1-4}$ alkylcarbonylamino groups (e.g. acetylamino, propionylamino, butyrylamino, etc.), $C_{1-4}$ alkylsulfonylamino groups (e.g. methylsulfonylamino, ethylsulfonylamino, etc.), $C_{1-4}$ alkoxy-carbonyl groups (e.g. methoxycarbonyl, ethoxycarbonyl, propoxycarbonyl, etc.), carboxyl, $C_{1-6}$ alkyl-carbonyl groups (e.g. methylcarbonyl, ethylcarbonyl, propylcarbonyl, etc.), carbamoyl, mono- or di-$C_{1-4}$ alkyl-carbamoyl groups (e.g. methylcarbamoyl, ethylcarbamoyl, etc.), $C_{1-6}$ alkylsulfonyl groups (e.g. methylsulfonyl, ethylsulfonyl, propylsulfonyl, etc.) and so on. 1 to 5, preferably 1 or 2, species of these substituents may be present.

The preferred examples of R are a hydrogen atom or a straight-chain or branched $C_{1-4}$ alkyl group (e.g. methyl, ethyl, n-propyl, n-butyl, etc.). And, the preferred examples of R are also a $C_{1-4}$ alkyl substituted with dimethylamino (e.g. dimethylaminomethyl, dimethylaminoethyl, etc.).

Referring, further, to the formulas presented hereinbefore, $R^1$ represents a hydrogen atom or an alkyl group which may be substituted. "The alkyl group" includes preferably a straight-chain or branched $C_{1-6}$ alkyl group, a $C_{3-6}$ cycloalkyl group or a cycloalkyl-$C_{1-4}$ alkyl group. The straight-chain or branched $C_{1-6}$ alkyl group mentioned above includes methyl, ethyl, propyl, isopropyl, butyl, isobutyl, sec-butyl, tert-butyl, pentyl, neopentyl, hexyl, etc. and may be preferably a straight-chain or branched $C_{1-4}$ alkyl group such as methyl, ethyl, propyl, isopropyl, butyl, isobutyl, sec-butyl, tert-butyl, etc. The $C_{3-6}$ cycloalkyl group may for example be cyclopropyl, cyclopentyl or cyclohexyl and so on. The $C_{3-6}$ cycloalkyl-$C_{1-4}$ alkyl group includes cyclopropylmethyl, cyclopropylethyl and so on.

The substituent group(s) optionally substituting said alkyl group for $R^1$ include the same substituent which indicate "the substituent" of "the alkyl group which may be substituted", which is represented by R, and a phenyl group.

The preferred examples of $R^1$ are a hydrogen atom or a $C_{1-4}$ alkyl group which may be substituted with phenyl (e.g. methyl, ethyl, propyl, isopropyl, butyl, isobutyl, benzyl, etc.).

The more preferred example of $R^1$ is a $C_{1-4}$ alkyl group (e.g. methyl, ethyl, propyl, isopropyl, etc.).

Referring, further, to the formulas presented hereinbefore, $R^2$ represents a hydrocarbon group which may be substituted or a heterocyclic group which may be substituted. The "hydrocarbon group" of the "hydrocarbon group which may be substituted", which is represented by $R^2$, includes alkyl, aryl and aralkyl groups. The preferable examples are aryl and aralkyl group, more preferably aralkyl group.

The alkyl group mentioned just above includes preferably a straight-chain or branched $C_{1-8}$ alkyl group, a $C_{3-6}$ cycloalkyl group or a $C_{3-6}$ cycloalkyl-$C_{1-4}$ alkyl group. The straight-chain or branched $C_{1-8}$ alkyl group includes methyl, ethyl, propyl, isopropyl, butyl, isobutyl, sec-butyl, tert-butyl, pentyl, isopentyl, neopentyl, hexyl, heptyl, octyl and so on. Particularly preferred is a straight-chain or branched $C_{1-6}$ alkyl group such as methyl, ethyl, propyl, isopropyl, butyl, isobutyl, sec-butyl, tert-butyl, pentyl, isopentyl, neopentyl, hexyl and so on. The $C_{3-6}$ cycloalkyl group includes cyclopropyl, cyclopentyl, cyclohexyl and so on. The $C_{3-6}$ cycloalkyl-$C_{1-4}$ alkyl groups include cyclopropylmethyl, cyclopropylethyl, cyclobutylmethyl, cyclopentylmethyl, cyclohexylmethyl and so on.

The aryl group mentioned above includes preferably a $C_{6-10}$ aryl group such as, for example, phenyl and naphthyl and more preferably a $C_{6-8}$ aryl group such as phenyl and so on.

The aralkyl group also mentioned above includes preferably a $C_{7-16}$ aralkyl group such as benzyl, 1-phenylethyl, 2-phenylethyl, 1-phenylpropyl, 2-phenylpropyl, 3-phenylpropyl, diphenylmethyl, 1-naphthylmethyl, 2-naphthylmethyl, etc. and more preferably a $C_{7-13}$ aralkyl group such as benzyl, 1-phenylethyl, 2-phenylethyl, 1-phenylpropyl, 2-phenylpropyl, 3-phenylpropyl, diphenylmethyl and so on. Particularly preferred are $C_{7-8}$ aralkyl groups such as benzyl, 1-phenylethyl and so on.

The hydrocarbon group represented by $R^2$ may have 1 to 5, preferably 1 to 3, substituent groups which may be the same or different. Among such substituent groups which may be exemplified are halogen atoms (e.g. fluoro, chloro, bromo, iodo, etc.), nitro, cyano, hydroxyl, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio, isopropylthio, butylthio, etc.), amino, mono- or di-$C_{1-4}$ alkylamino groups (e.g. methylamino, ethylamino, propylamino, dimethylamino, diethylamino, etc.), cyclic amino groups (e.g. 5- to 9-membered cyclic amino groups which may contain 1 to 3 hetero-atoms such as oxygen and sulfur in addition to nitrogen as ring-constituent members, such as pyrrolidino, piperidino, morpholino, etc.), $C_{1-4}$ alkylcarbonylamino groups (e.g. acetylamino, propionylamino, butyrylamino, etc.), aminocarbonyloxy group, mono- or di-$C_{1-4}$ alkylaminocarbonyloxy groups (e.g. methylaminocarbonyloxy, ethylaminocarbonyloxy, dimethylaminocarbonyloxy, diethylaminocarbonyloxy, etc.), $C_{1-4}$ alkylsulfonylamino groups (e.g. methylsulfonylamino, ethylsulfonylamino, propylsulfonylamino, etc.), $C_{1-4}$ alkoxy-carbonyl groups (e.g. methoxycarbonyl, ethoxycarbonyl, propoxycarbonyl, isobutoxycarbonyl, etc.), benzyloxycarbonyl group, carboxyl, $C_{1-6}$ alkylcarbonyl groups (e.g. methylcarbonyl, ethylcarbonyl, butylcarbonyl, etc.), $C_{3-6}$ cycloalkyl-carbonyl groups (e.g. cyclohexylcarbonyl etc.), carbamoyl, mono- or di-$C_{1-4}$ alkyl-carbamoyl groups (e.g. methylcarbamoyl, ethylcarbamoyl, propylcarbamoyl, butylcarbamoyl, diethylcarbamoyl, dibutylcarbamoyl, etc.), $C_{1-6}$ alkylsulfonyl groups (e.g. methylsulfonyl, ethylsulfonyl, propylsulfonyl, etc.) and so on. Furthermore, the "heterocyclic group which may be substituted", represented by $R^2$, which is described in detail hereinafter, can be used as a substituent for this hydrocarbon group. This heterocyclic group which may be substituted includes, among others, 5- or 6-membered aromatic monocyclic heterocyclic groups (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiazolyl, 1,2,4-thiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.) which may be substituted with 1 to 3 substituents selected from, for example, $C_{1-4}$ alkyl groups (e.g. methyl, ethyl, propyl, butyl, etc.), $C_{3-6}$ cycloalkyl groups (e.g. cyclopropyl, cyclobutyl, cyclopentyl, cyclohexyl, etc.), halogen atoms (e.g. fluoro, chloro, bromo, iodo, etc.), hydroxyl, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio, isopropylthio, butylthio, etc.), amino, mono- or di-$C_{1-4}$ aminoalkyl groups (e.g. methylamino, ethylamino, propylamino, dimethylamino, diethylamino, etc.), $C_{1-4}$ alkoxy-carbonyl groups (e.g. methoxycarbonyl, ethoxycarbonyl, propoxycarbonyl, isobutoxycarbonyl, etc.), carboxyl, $C_{1-6}$ alkyl-carbonyl groups (e.g. methylcarbonyl, ethylcarbonyl, butylcarbonyl, etc.) and so on. When the hydrocarbon group $R^2$ is a $C_{3-6}$ cycloalkyl group, an aryl group or an aralkyl group, it may be substituted by $C_{1-4}$ alkyl (e.g. methyl, ethyl, propyl, butyl, etc.).

The "heterocyclic group" of the "heterocyclic group which may be substituted", which is represented by $R^2$, includes a variety of 5- to 9-membered, preferably 5- or 6-membered, aromatic or non-aromatic heterocyclic groups containing 1 to 4, preferably 1 or 2, hetero-atoms such as nitrogen, oxygen and/or sulfur in addition to carbon.

The aromatic heterocyclic groups mentioned above include aromatic monocyclic heterocyclic groups such as furyl, thienyl, pyrrolyl, oxazolyl, isoxazolyl, thiazolyl, isothiazolyl, imidazolyl, pyrazolyl, thiophenyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc. and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and so on.

The non-aromatic heterocyclic groups mentioned above include, among others, oxiranyl, azetidinyl, oxetanyl, pyrrolidinyl, tetrahydrofuryl, thiolanyl, piperidyl, tetrahydropyranyl, morpholinyl, thiomorpholinyl, pyrazinyl and so on.

Among the above heterocyclic groups, 5- or 6-membered heterocyclic groups are preferred and, for example, furyl, thienyl, pyrrolyl, oxazolyl, isoxazolyl, imidazolyl, pyrazolyl, pyridyl, pyridazinyl, quinolyl, isoquinolyl, thiazolyl, thiadiazolyl, thiophenyl, etc. can be employed with advantage. Particularly useful are thiazolyl and thiadiazolyl.

The "substituent(s)" of said "heterocyclic group which may be substituted", which is represented by $R^2$, are 1 to 3 substituents selected from the group consisting of $C_{1-4}$ alkyl groups (e.g. methyl, ethyl, propyl, butyl, etc.), $C_{3-6}$ cycloalkyl groups (e.g. cyclopropyl, cyclobutyl, cyclopentyl, cyclohexyl, etc.), halogen atoms (e.g. fluoro, chloro, bromo, iodo, etc.), nitro, cyano, hydroxyl, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio, isopropylthio, butylthio, etc.), amino, mono- or di-$C_{1-4}$ alkylamino groups (e.g. methylamino, ethylamino, propylamino, dimethylamino, diethylamino, etc.), cyclic amino groups (e.g. 5- to 9-membered cyclic amino groups which may contain 1 to 3 hetero-atoms such as oxygen and sulfur in addition to nitrogen as ring-constituent members, such as pyrrolidino, piperidino, morpholino, etc.), $C_{1-4}$ alkylcarbonylamino groups (e.g. acetylamino, propionylamino, butyrylamino, etc.), aminocarbonyloxy, mono- or di-$C_{1-4}$ alkylaminocarbonyloxy groups (e.g. methylaminocarbonyloxy, ethylaminocarbonyloxy, dimethylaminocarbonyloxy, diethylaminocarbonyloxy, etc.), $C_{1-4}$ alkylsulfonylamino groups (e.g. methylsulfonylamino, ethylsulfonylamino, propylsulfonylamino, etc.), $C_{1-4}$ alkoxy-carbonyl groups (e.g. methoxycarbonyl, ethoxycarbonyl, propoxycarbonyl, isobutoxycarbonyl, etc.), carboxyl, $C_{1-6}$ alkyl-carbonyl groups (e.g. methylcarbonyl, ethylcarbonyl, butylcarbonyl, etc.), $C_{3-6}$ cycloalkyl-carbonyl groups (e.g. cyclohexylcarbonyl etc.), carbamoyl, mono- or di-$C_{1-4}$ alkyl-carbamoyl groups (e.g. methylcarbamoyl, ethylcarbamoyl, propylcarbamoyl, butylcarbamoyl, diethylcarbamoyl, dibutylcarbamoyl, etc.), $C_{1-6}$ alkylsulfonyl groups (e.g. methylsulfonyl, ethylsulfonyl, propylsulfonyl, etc.), $C_{3-6}$ cycloalkylsulfonyl groups (e.g. cyclopentylsulfonyl, cyclohexylsulfonyl, etc.), and a phenyl, naphthyl, phenoxy, benzoyl, phenoxycarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may have 1 to 4 substituent groups (the substituent groups on the phenyl or naphthyl group include, among others, $C_{1-4}$ alkyl groups such as methyl, ethyl, propyl, butyl, isopropyl, etc., $C_{1-4}$ alkoxy groups such as methoxy, ethoxy, n-propyloxy, i-propyloxy, n-butyloxy, etc., halogen atoms such as chloro, bromo, iodo, etc., hydroxyl, benzyloxy, amino, mono- or di-$C_{1-4}$ alkylamino groups such as those mentioned hereinbefore, nitro and $C_{1-6}$ alkylcarbonyl groups such as those mentioned hereinbefore).

Preferably, $R^2$ is (1) a phenyl or $C_{7-8}$ aralkyl (e.g. benzyl, 1-phenylethyl, etc.) group which may have 1 to 3 substituent groups such as, for example, halogen atoms (e.g. fluoro, chloro, etc.), $C_{1-4}$ alkyl groups (e.g. methyl, ethyl, etc.), $C_{1-4}$ alkoxy groups (e.g. methoxy, ethoxy, propyloxy, isopropyloxy, etc.), etc., (2) a $C_{3-7}$ cycloalkylmethyl group (e.g. cyclohexylmethyl etc.), (3) a $C_{1-8}$ alkyl group such as methyl substituted by a heterocyclic group such as 5- or 6-membered heterocyclic group which may contain 1 to 3 hetero-atoms (e.g. nitrogen, oxygen, sulfur, etc.) in addition to carbon (e.g. furylmethyl, pyridylmethyl, thienylmethyl, etc.) or (4) a 5- or 6-membered heterocyclic group which contains 1 to 3 hetero-atoms (e.g. nitrogen, oxygen, sulfur, etc.) in addition to carbon (e.g. furyl, pyridyl, thienyl, thiazolyl, thiadiazolyl, etc.) and may be substituted by a $C_{1-4}$ alkyl (e.g. methyl, ethyl, etc.) or $C_{3-7}$ cycloalkyl (e.g. cyclopropyl, etc.).

$R^1$ and $R^2$, taken together with the adjacent nitrogen atom, may form a ring which may be substituted. The "ring" of this "ring which may be substituted" may for example be a nitrogen-containing heterocycle containing 1 to 3 heteroatoms selected from among nitrogen, oxygen, sulfur, etc. in addition to the nitrogen and carbon and particularly a 3- to 13-membered nitrogen-containing heterocycle. Specifically, it can be any of saturated monocyclic, non-conjugated unsaturated monocyclic, unsaturated monocyclic, polycyclic and bridged ring heterocyclic systems.

The saturated monocyclic heterocycle includes 5- to 9-membered monocyclic heterocycles such as pyrrolidine, piperidine, hexamethyleneimine, heptamethyleneimine, oxazolidine, morpholine, thiazolidine, thiomorpholine, imidazolidine, piperazine, homopiperazine and so on.

The non-conjugated unsaturated monocyclic or unsaturated monocyclic heterocycle includes 5- to 9-membered non-conjugated monocyclic or unsaturated monocyclic heterocycles such as pyrrole, 1,2-dihydropyridine, 1,4-dihydropyridine, 1,2,3,6-tetrahydropyridine, 2-oxazolidone, 2-thiazolidone, imidazole, pyrazole, 1,4,5,6-tetrahydropyrimidine and so on.

The polycyclic heterocycle mentioned above includes such polyclic heterocycles as 2,3-dihydro-1H-indole, 1,2,3, 4-tetrahydroquinoline, 2,3,4,5-tetrahydro-1H-1-benzazepine, 2,3-dihydro-1H-isoindole, 1,2,3,4-tetrahydroisoquinoline, 2,3,4,5-tetrahydro-1H-2-benzazepine, 2,3,4,5-tetrahydro-1H-3-benzazepine, 1,2,3,4,5,6-hexahydro-1-benzazocine, 1,2,3,4,5,6-hexahydro-2-benzazocine, 1,2,3,4, 5,6-hexahydro-3-benzazocine, 2,3,4,5,6,7-hexahydro-1H-1-benzazonine, 2,3,4,5,6,7-hexahydro-1H-2-benzazonine, 2,3, 4,5,6,7-hexahydro-1H-3-benzazonine, 2,3,4,5,6,7-hexahydro-1H-4-benzazonine, β-carboline, phenoxazine, phenothiazine, indole, 3H-3-benzazepine, 3,4-dihydroquinoline, benzimidazole, 1,4-benzodiazepine and so on.

The bridged ring heterocycle includes such bridged ring heterocycles as 1,8-diazaspiro[4,5]decane, 2,8-diazaspiro[4, 5]decane, 1,3,8-triazaspiro[4,5]decane, 1,5,9-triazaspiro[5, 5]undecane, 1-oxa-3,9-diazaspiro[5,5]undecane, 7-azabicyclo[2,2,1]heptane, 8-azabicyclo[3,2,1octane, 9-azabicyclo [3,3,1]nonane and so on.

The "ring" of the "ring which may be substituted", which $R^1$ and $R^2$ may jointly form with the adjacent nitrogen atom is preferably a saturated monocyclic heterocycle such as those mentioned above. Specifically, pyrrolidine, piperidine, piperazine, morpholine, etc. and more particularly piperidine and piperazine are preferred.

The "substituent" on the "ring which may be substituted", which $R^1$ and $R^2$ may form with the adjacent nitrogen atom, may for example be a hydrocarbon group which may be substituted or a heterocyclic group which may be substituted, which has hereinbefore mentioned for $R^2$.

The "ring which may be substituted" which $R^1$ and $R^2$ may form with the adjacent nitrogen atom may be preferably a ring of the formula:

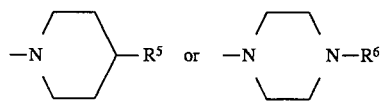

wherein $R^5$ and $R^6$ each means a hydrocarbon group which may be substituted or a heterocyclic group which may be substituted.

In the above formula, the hydrocarbon group which may be substituted and the heterocyclic group which may be substituted, each as represented by $R^5$ and $R^6$, may for example be the hydrocarbon group which may be substituted and the heterocyclic group which may be substituted, which have hereinbefore mentioned for $R^2$.

As the preferred examples of $R^5$ and $R^6$ may be exemplified hydrocarbon groups, particularly $C_{6-10}$ aryl groups such as phenyl, and $C_{7-8}$ aralkyl groups such as benzyl.

When, in the compound (I) of the present invention, $R^1$ is a hydrogen and $R^2$ is a phenyl substituted with halogen such as two fluoro atoms, for example, the moiety

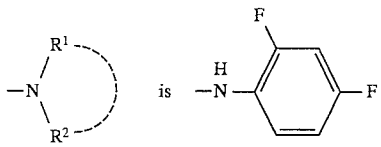

it is preferable that ring A is a benzene ring substituted by two alkyl such as $C_{1-4}$ alkyl group or two halogen atoms and ring B is a benzene ring which may be substituted by a halogen. When $R^1$ is a hydrogen and $R^2$ is a phenyl substituted with alkyl such as $C_{1-4}$ alkyl in the compound (I), for example, the moiety

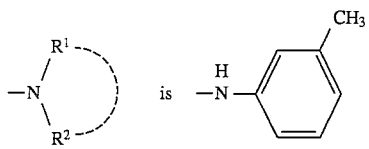

ring A is preferably a benzene ring substituted by two alkyl such as $C_{1-4}$ alkyl groups or two halogen atoms and ring B is a benzene ring which may be substituted by a halogen.

The compound (I) of the present invention in which $R^2$ is a heterocyclic group which may be substituted or an alkyl group substituted by a heterocyclic group which may be substituted, or a salt thereof, is particularly useful.

Also preferred is the compound (I) of the formula:

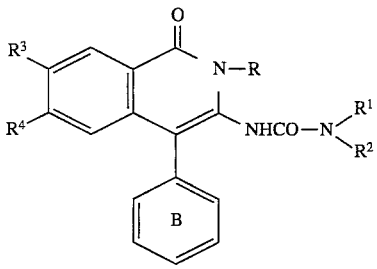

wherein $R^3$ and $R^4$ each represents an alkyl group; the other symbols are as defined hereinbefore, or a salt thereof.

Referring to the above formula ($I^b$), the alkyl group $R^3$, $R^4$ is preferably a straight-chain or branched $C_{1-6}$ alkyl group, a $C_{3-6}$ cycloalkyl group or a $C_{3-6}$ cycloalkyl-$C_{1-4}$ alkyl group. The straight-chain or branched $C_{1-6}$ alkyl group mentioned above includes methyl, ethyl, propyl, isopropyl, butyl, isobutyl, sec-butyl, tert-butyl, pentyl, neopentyl, hexyl, etc., and straight-chain or branched $C_{1-4}$ alkyl groups such as methyl, ethyl, propyl, isopropyl butyl, isobutyl, sec-butyl, tert-butyl, etc. are particularly preferred. The $C_{3-6}$ cycloalkyl group may for example be cyclopropyl, cyclopentyl or cyclohexyl. The $C_{3-6}$ cycloalkyl-$C_{1-4}$ alkyl group includes cyclopropyl methyl, cyclopropyl ethyl and so on.

Among various species of the above compound ($I^b$) or salts thereof, compounds meeting at least one of the following conditions (1)–(6) are particularly useful.

(1) $R^3$ and $R^4$ each is a straight-chain or branched $C_{1-4}$ alkyl group, such as methyl, ethyl, propyl, isopropyl, butyl, isobutyl, etc., and preferably methyl.

(2) Ring B is a benzene ring which may be substituted by a halogen (e.g. fluoro, chloro, etc.)

(3) R is a $C_{1-4}$ alkyl such as methyl (4) $R^2$ is an aralkyl group which may be substituted, particularly a $C_{7-8}$ aralkyl group (e.g. benzyl, 2-phenylethyl, etc.) which may have 1 or 2 substituents selected from among a halogen (e.g. fluoro, chloro, etc.), a $C_{1-4}$ alkoxy (e.g. methoxy, ethoxy, etc.) and so on.

(5) Ring B is an unsubstituted benzene ring and $R^2$ is a substituted phenyl group, particularly phenyl having 1 or 2 substituents selected from among a halogen (e.g. fluoro, chloro, etc.), a $C_{1-4}$ alkyl (e.g. methyl, ethyl, etc.), a $C_{1-4}$ alkoxy (e.g. methoxy, ethoxy, etc.) and so on.

(6) $R^1$ is a $C_{1-6}$ alkyl group substituted by a heterocyclic group which may be substituted (e.g. thiazolyl or thiadiazolyl which may be substituted with a $C_{1-4}$ alkyl or a $C_{3-7}$ cycloalkyl, such as thiazolyl, methylthiazolyl, methylthiadiazolyl, cyclopropylthiadiazolyl, etc.).

Preferred examples of compounds ($I^b$) or salts thereof may meet two or more of the above conditions as follows.

1. (1) and (4).
2. (1), (2) and (4).
3. (1), (3) and (4).
4. (1), (2), (3) and (4).
5. (1) and (5).
6. (1), (3) and (5).

The salt of compound (I) according to the present invention is preferably a physiologically acceptable acid addition salt. Examples of such salt include salts with inorganic acids (e.g. hydrochloric acid, phosphoric acid, hydrobromic acid, sulfuric acid, etc.) and salts with organic acids (e.g acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). When the compounds (I) of the invention have an acidic group such as —COOH, the compounds (I) may form salts with inorganic bases (e.g. alkali metal or alkaline earth metals such as sodium, potassium, magnesium, etc.; ammonia) or salts with organic bases (e.g. tri-$C_{1-3}$ alkylamine such as triethylamine).

The method for producing the compound (I) and salt of the present invention is now described.

The compound (I) or a salt thereof can be produced, for example by the following alternative processes (1) and (2).

Thus, compound (I) or a salt thereof can be synthesized by:

(1) reacting a heterocyclic isocyanate of general formula (II) or a salt thereof with an amine of general formula (III) or a salt thereof, or (2) reacting a heterocyclic amine of general formula (IV) or a salt thereof with a substituted aminocarboxylic acid of general formula (V) or a salt thereof or a reactive derivative of the carboxyl group thereof.

The above processes (1) and (2) are now described in detail.

Process (1): When compound (II) or a salt thereof is reacted with compound (III) or a salt thereof [the salt of (II) and the salt of (III) may each be the corresponding salt with an inorganic acid such as hydrochloric acid, sulfuric acid, etc. or an organic acid such as methanesulfonic acid, benzenesulfonic acid, toluenesulfonic acid, oxalic acid, fumaric acid, maleic acid, etc.]. The compound (III) as such can be used as the solvent but the reaction can be conducted using a different solvent as well. Any solvent can be used that does not interfere with the reaction. Thus, various ethers (e.g. diethyl ether, diisopropyl ether, tetrahydrofuran, dioxane, dimethoxyethane, etc.), aromatic hydrocarbons (e.g. benzene, toluene, xylene, etc.), esters (e.g. methyl acetate, ethyl acetate, etc.), amides (e.g. N,N-dimethylformamide etc.) and sulfoxides (e.g. dimethyl sulfoxide etc.), for instance, can be employed with advantage. When compound (III) is used in the form of a salt, the reaction can be conducted with advantage in the presence of a desalting agent. The preferred desalting agent includes tertiary amines such as trimethylamine, triethylamine, N-methylmorpholine, etc. and aromatic amines such as pyridine, picoline, N,N-dimethylaniline and so on. The amount of such desalting agent is 1 to 5 mol equivalents, preferably 1 to 3 mol equivalents, per mole of the salt of compound (III). The reaction temperature is generally −10° C. to 180° C. and preferably 0° C. to 120° C. The reaction time is generally 15 minutes to 40 hours and preferably 30 minutes to 20 hours. The proportion of compound (III) or its salt is 1 to 5 mol equivalents, preferably 1 to 3 mol equivalents, per mol of compound (II) or a salt thereof.

Process (2): The reaction of a substituted aminocarboxylic acid of general formula (V) or a salt or reactive derivative thereof with compound (IV) or a salt thereof is an amide bond-forming reaction and can be carried out in a variety of ways. For example, when compound (IV) or a salt thereof (e.g. The corresponding salt with an inorganic acid such as hydrochloric acid, sulfuric acid, etc. or an organic acid such as methanesulfonic acid, benzenesulfonic acid, toluenesulfonic acid, oxalic acid, fumaric acid, maleic acid, etc.) is reacted with compound (V) or a salt thereof (e.g. the corresponding salt with an alkali or alkaline earth metal such as sodium, potassium, magnesium, etc.), it is advisable to employ a suitable condensing agent or to convert compound (V) or a salt thereof to a reactive derivative in the first place in a conventional manner and then react the derivative with compound (IV) or a salt thereof. The condensing agent that can be used for this purpose includes dicyclohexylcarbodiimide (DCC), diethyl cyanophosphate (DEPC), diphenylphosphorylazide (DPPA) and so on. When such a condensing agent is employed, the reaction is preferably conducted in a solvent (e.g. ethers, esters, hydrocarbons, amides and sulfoxides, such as tetrahydrofuran, dioxane, dimethoxyethane, ethyl acetate, benzene, toluene, N,N-dimethylformamide, dimethyl sulfoxide, etc.). This reaction can be accelerated by conducting it in the presence of a base. This reaction is carried out generally at about −10° C. to 100° C. and preferably about 0° C. to 60° C. The reaction time is generally 1 to 96 hours and preferably 1 to 72 hours. The proportion of compound (V) or a salt thereof and that of the condensing agent are generally 1 to 5 mol equivalents each, preferably 1 to 3 mol equivalents each, relative to each mol of compound (IV) or a salt thereof. The base that can be used includes alkylamines such as triethylamine etc. and cyclic amines such as N-methylmorpholine, pyridine, etc., among others. The proportion of the base per mol of compound (IV) or a salt thereof is 1 to 5 mol equivalents and preferably 1 to 3 mol equivalents.

The reactive derivative of compound (V) includes, among others, acid halides (e.g. chloride, bromide, etc.), acid anhydride, mixed acid anhydrides (e.g. anhydride with monomethyl carbonate, anhydride with monoethyl carbonate, anhydride with monoisobutyl carbonate, etc.), active esters (e.g. hydroxysuccinimide ester, 1-hydroxybenzotriazole ester, N-hydroxy-5-norbornene-2,3-dicarboxyimide ester, p-nitrophenol ester, 8-oxyquinoline ester, etc.) and so on. Particularly preferred are acid halides (e.g. chloride, bromide, etc.). When compound (IV) or a salt thereof is reacted with such a reactive derivative of compound (V), the reaction is generally conducted in a solvent (e.g. halogenated hydrocarbons, ethers, esters, hydrocarbons, amides, etc., such as chloroform, dichloromethane, ethyl ether, tetrahydrofuran, dioxane, dimethoxyethane, ethyl acetate, benzene, toluene, pyridine, N,N-dimethylformamide, etc.). This reaction can be accelerated by conducting it in the presence of a base. The reaction temperature is generally about −10° C. to 120° C. and preferably about 0° C. to 100° C. The reaction time is generally 1 to 48 hours and preferably 1 to 24 hours. The proportion of the reactive derivative of compound (V) to each mol of compound (IV) or a salt thereof is generally 1 to 5 mol equivalents and preferably 1 to 3 mol equivalents. The base which can be used includes, among others, alkylamines such as triethylamine etc., cyclic amines such as N-methylmorpholine, pyridine, etc., aromatic amines such as N,N-dimethylaniline, N,N-diethylaniline, etc., alkali metal carbonates such as sodium carbonate, potassium carbonate, etc. and alkali metal hydrogen carbonates such as sodium hydrogen carbonate, potassium hydrogen carbonate, etc. and the proportion thereof is 1 to 5 ml equivalents, preferably 1 to 3 mol equivalents, per mol of compound (IV) or a salt thereof. When the reaction solvent is immiscible with water, water may be added to the reaction system to conduct the reaction in a biphasic solvent system.

When the compound (I) or salt obtained by either of the above processes (1) and (2) has a lower ($C_{1-6}$) alkoxy group on any benzene ring among ring A, ring B and $R^2$, it can be treated with boron tribromide or the like to convert said group to a hydroxyl group as required. This reaction is generally conducted in a solvent (e.g. a halogenated hydrocarbon or a hydrocarbon, such as dichloromethane, chloroform, carbon tetrachloride, benzene, toluene, etc.) at a temperature of about −20° C. to 80° C. and preferably about 0° C. to 30° C. The amount of boron tribromide is about 1 to 10 mol equivalents, preferably about 1 to 5 mol equivalents, relative to the lower alkoxy group. The reaction time is generally 15 minutes to 24 hours and preferably 30 minutes to 12 hours. When the compound (I) or salt produced by either of the above processes (1) and (2) contains a hydroxyl group on any benzene ring among ring A, ring B and $R^2$, it can be converted to an alkoxy or acyloxy group, as required, by alkylation or acylation. This alkylation reaction is carried out using an alkylating agent such as the halide (e.g. chloride, bromide, iodide, etc.), sulfate ester or sulfonate ester (e.g. methanesulfonate, p-toluenesulfonate, benzensulfonate, etc.) of an optionally substituted alkane in the presence of a base (such as an organic base, e.g. trimethylamine, triethylamine, N-methylmorpholine, pyridine, picoline, N,N-dimethylaniline, etc. or an inorganic base, e.g. potassium carbonate, sodium carbonate, potassium hydroxide, sodium hydroxide, etc.) in a solvent (such as an alcohol, e.g. methanol, ethanol, propanol, etc., an ether, e.g. dimethoxyethane, dioxane, tetrahydrofuran, etc., a ketone, e.g. acetone etc., or an amide, e.g. N,N-dimethylformamide etc.). The reaction temperature is generally −10° C. to 100° C. and preferably about 0° C. to 80° C. The amount of such alkylating agent is about 1 to 5 mol equivalents, preferably about 1 to 3 mol equivalents, per mol of the starting material phenolic derivative. The reaction time is generally 15 minutes to 24 hours and preferably 30 minutes to 12 hours.

The acylation reaction is carried out using an optional carboxylic acids or a reactive derivative thereof. While the reaction conditions vary with the kind of acylating agent and that of the starting material phenolic derivative, this acylation reaction is generally conducted in a solvent (e.g. hydrocarbons, ethers, esters, halogenated hydrocarbons, amides and aromatic amines, such as benzene, toluene, ethyl ether, ethyl acetate, chloroform, dichloromethane, dioxane, tetrahydrofuran, N,N-dimethylformamide, pyridine, etc.), optionally in the presence of a suitable base (e.g. hydrogen carbonates such as sodium hydrogen carbonate, potassium hydrogen carbonate, etc., carbonates such as sodium carbonate, potassium carbonate, etc., acetates such as sodium acetate etc., tertiary amines such as triethylamine etc., and aromatic amines such as pyridine etc.) as an accelerator of reaction. The reactive derivative of such carboxylic acid may for example be the corresponding acid anhydride, mixed acid anhydrides or acid halide (e.g. chloride, bromide, etc.). The amount of the acylating agent is 1 to 5 mol equivalents, preferably 1 to 3 mol equivalents, per mol of the starting material phenolic derivative. The reaction temperature is generally 0° C. to 150° C. and preferably about 10° C. to 100° C. The reaction time is generally 15 minutes to 12 hours and preferably 30 minutes to 6 hours.

When the compound (I) is obtained in the free form, it can be converted to a salt, such as mentioned above, by the per se known procedure or a procedure analogous thereto, while the compound (I) obtained in the form of a salt can be converted to the free form or a different salt by a per se known procedure or any procedure analogous thereto.

The objective compound (I) or salt thus obtained can be isolated and purified by the per se known procedure (e.g. concentration, solvent extraction, column chromatography, recrystallization, etc.)

The starting compounds (II) and (IV), inclusive of salts thereof, which are used in the production of the compound (I) or salt of the present invention can be produced advantageously on a commercial scale by the process described below (reaction schema 1) or any process analogous thereto.

[Reaction Schema 1]

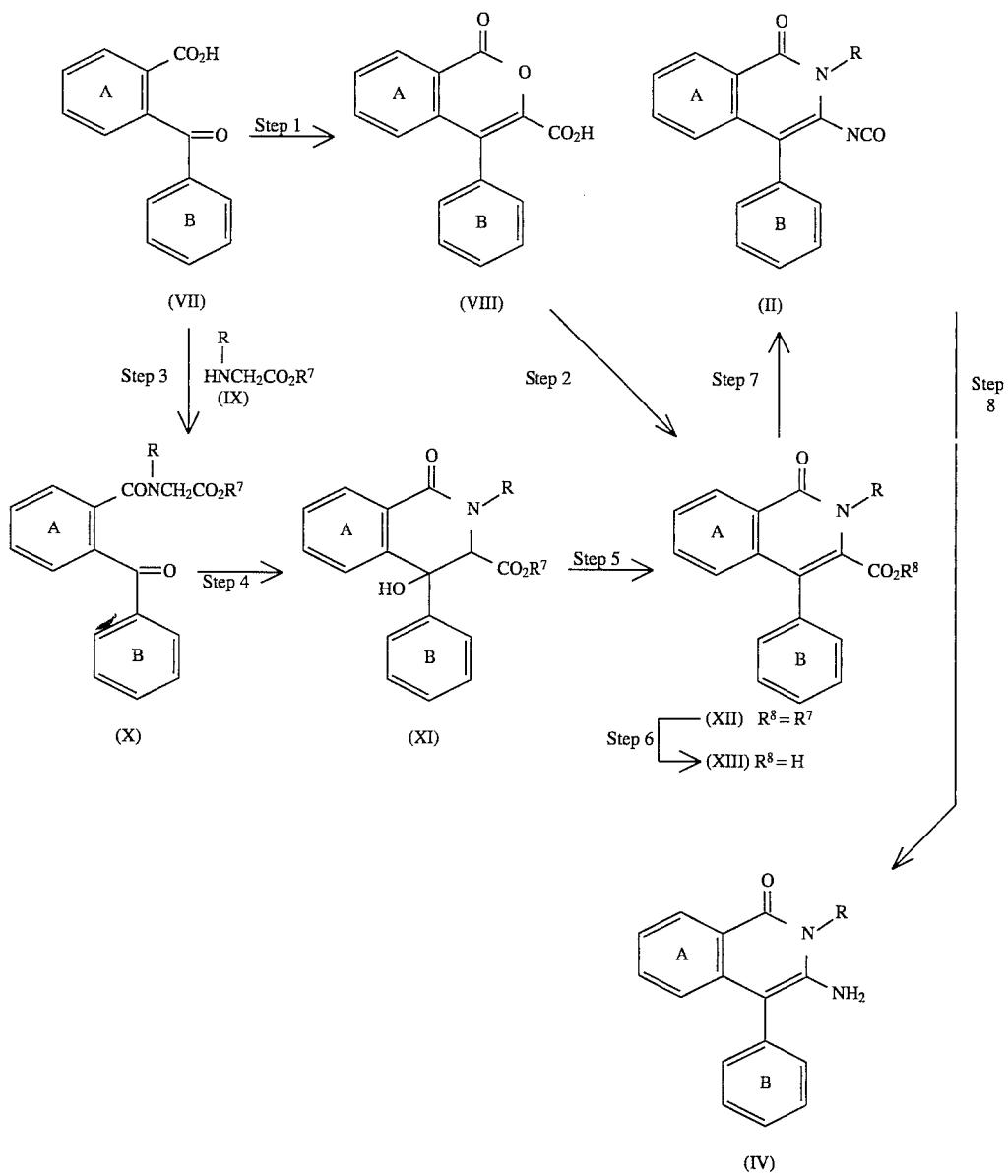

wherein ring A, ring B and R are as defined hereinbefore; $R^7$ represents a carboxyl-protecting group; $R^8$ represents hydrogen or a carboxyl-protecting group.

In the above reaction schema, a 2-benzoylbenzoic acid derivative of formula (VII) is used as the starting material.

Step 1 is a reaction for the production of 4-phenylisocoumarin-3-carboxylic acid (VIII) and this reaction can be carried out by a known procedure [e.g. F. Duro and P. Condorelli, Boll. Acad. Gioenia Sci. Nat. Catania, Vol 5, p 606, 1960] or any procedure analogous thereto.

Step 2 relates to the conversion of compound (VIII) to isoquinolonecarboxylic acid (XIII) and this reaction can be carried out by a known procedure [e.g. N. A. Santagati, E. Bousquet, G. Romeo, A. Garuso and A. Prato, Bolletino Chimico Farmaceutico, Vol 125, p437, 1986] or any procedure analogous thereto.

This isoquinolonecarboxylic acid (XIII) can also be produced from compound (VII) via Steps 3 through 6.

Thus, Step 3 is a process for producing an amide (X) through reaction between the carboxyl group of compound (VII) and the amino group of glycine derivative (IX). This reaction of compound (VII) or a reactive derivative of the carboxyl group thereof with compound (IX) can be conducted under the same conditions as the reaction (Process (2)) between said compounds (IV) and (V) for the production of compound (I).

Step 4 comprises treating compound (X) with a base to give a cyclized compound (XI) through intramolecular addition reaction. The base which can be used with advantage for this reaction includes organic bases such as 1,5-diazabicyclo[4.3.0]non-5-ene (DBN), 1,8-diazabicyclo[5.4.0]undec-7-ene (DBU), N-benzyltrimethylammonium hydroxide (Triton B), etc. and inorganic bases such as sodium methoxide, sodium ethoxide, potassium t-butoxide, sodium hydride, potassium hydride, n-butyllithium, lithium diisopropylamide, etc., although the bases which can be used in the reaction between compounds (IV) and (V) (Process (2)) may also be employed. The amount of the base is generally 0.5 to 20 equivalents and preferably 1 to 5 equivalents. This reaction is generally carried out in a solvent. For this purpose, solvents which can be used in the reaction between compounds (IV) and (V) (process (2)) are also usable. While the reaction temperature is dependent on the base used, this reaction is carried out generally at about $-80°$ C. to $200°$ C. and preferably at about $-50°$ C. to $150°$ C. The reaction time, which is also dependent on the species of starting compound, base and solvent as well as on the reaction temperature, is generally in the range of about 10 minutes to 24 hours.

Step 5 comprises subjecting compound (XI) to dehydration reaction to provide an isoquinolone derivative (XII).

Generally, this reaction is preferably conducted in the presence of an acidic catalyst. The acidic catalyst that can be employed includes, among others, sulfonic acid compounds such as p-toluenesulfonic acid, methanesulfonic acid, etc., carboxylic acid compounds such as acetic acid, trifluoroacetic acid, etc., inorganic acid compounds such as hydrochloric acid, hydrobromic acid, sulfuric acid, etc. and Lewis acid compounds such as boron trifluoride ethyl ether, aluminum chloride and so on. The proportion of the acidic catalyst is 0.1 to 20 equivalents, preferably 0.1 to 5 equivalents, relative to compound (XI). This reaction is generally carried out in a solvent. The solvent may be any of those which can be used in the reaction between compounds (IV) and (V) (Process (2)). The reaction temperature varies with the species of catalyst used but is generally about $-10°$ C. to $200°$ C. and preferably $0°$ C. to $150°$ C. The reaction time, which also depends on the species of starting compound, base and solvent as well as on the reaction temperature, is generally about 30 minutes to 24 hours.

There are cases in which a dehydrative cyclization product (XII) is obtained in Step 4 depending on the species of compound (X), base or solvent or according to the reaction temperature and time.

In Step 6, the protective group $R^8$ is removed from the carboxyl group of compound (XII) to give compound (XIII).

This reaction can be carried out by various procedures according to the species of $R^8$ of (XII) [e.g. T. W. Greene, Protective Groups in Organic Synthesis, John Wiley & Sons, New York, 1981, p 157–187]. When, for example, the protective group on (XII) is a lower alkyl group such as methyl or ethyl, it can be eliminated, for example under hydrolysis conditions such as described below for Step 8.

In Step 7, isoquinolonecarboxylic acid (XIII) is converted to isocyanate (II).

The commonest route is via the acid azide and while many processes can be found in the literature, any of such processes can be applied to compound (XIII).

For example, the acid azide of compound (XIII) can be prepared by reacting compound (XIII) with an azide-forming agent [e.g. diphenylphosphorylazide (hereinafter referred to briefly as DPPA), etc.]. This reaction can be generally carried out in an inert solvent (e.g. ethers such as ethyl ether, isopropyl ether, dimethoxyethane, tetrahydrofuran, dioxane, etc., aromatic hydrocarbons such as benzene, toluene, xylene, etc., esters such as methyl acetate, ethyl acetate, etc., ketones such as acetone, 2-butsnone, etc., aromatic amines such as pyridine etc., and amides such as N,N-dimethylformamide etc.). To accelerate its progress, the reaction may be conducted in the presence of a base (e.g. trimethylamine, triethylamine, N-methylmorpholine, etc.). The reaction time is generally about 5 minutes to 12 hours and preferably about 10 minutes to 6 hours. The reaction temperature is generally about $-10°$ C. to $150°$ C. and preferably about $-5°$ C. to $120°$ C. The proportion of the azide-forming agent (e.g. DPPA) is 1 to 3 mol equivalents, preferably 1 to 2 mol equivalents, relative to compound (XIII).

While the acid azide thus obtained can be isolated and purified by the per se known procedure, the reaction mixture may be directly heated to convert the azide to isocyanate (II). This conversion reaction is preferably conducted in a solvent similar to that used in the azide-forming reaction and is carried out generally at about $20°$ C. to $200°$ C., preferably at about $30°$ C. to $150°$ C. The reaction time is generally about 5 minutes to 10 hours and preferably about 5 minutes to 6 hours. The resulting compound (II) is isolated by the per se known procedure or the reaction mixture is directly used for the production of compound (I) or (IV).

Step 8 is a reaction by which the isocyanato group of compound (II) is converted to an amine group to provide compound (IV). This step is generally carried out under hydrolysis conditions. This reaction can be conducted in a solvent (e.g. alcohols such as methanol, ethanol, propanol, butanol, etc., ethers such as tetrahydrofuran, dioxane, dimethyloxyethane, etc., and mixtures thereof), either under alkaline conditions in the presence of an alkali or alkaline earth metal hydroxide, e.g. sodium hydroxide, barium hydroxide, etc., or under acidic conditions in the presence of an inorganic acid, e.g. hydrochloric acid, hydrobromic acid, sulfuric acid, etc. The reaction temperature is generally about $0°$ C. to $120°$ C. and preferably about $15°$ C. to $100°$ C. The reaction time is about 30 minutes to 36 hours and preferably about 1 hour to 20 hours.

The starting compound (VII) shown in the above reaction schema can also be produced by the known process [e.g. P. Aeberli, P. Eden, J. H. Gogerty, W. J. Houlihan, and C. Penberthy, J. Med. Chem., 18, 177 (1975)] or any process analogous thereto.

Compound (III) and (V) can each be produced by the known method or any process analogous thereto.

The above-mentioned compounds (IV), (V), (VI), (VII), (VIII), (IX), (X), (XI), (XII) and (XIII) may each be in the form of a salt. The salt includes the corresponding salt with an inorganic acid (e.g. hydrochloric acid, phosphoric acid, hydrobromic acid, sulfuric acid, etc.) or with an organic acid (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). When any of these compounds has an acidic group such as —COOH, it may form a salt with an inorganic base (e.g. an alkali metal or alkaline earth metal, such as sodium, potassium, calcium, magnesium, etc.; ammonia) or an organic base (e.g. tri-$C_{1-3}$ alkylamine such as triethylamine).

The compound obtained in each of Step 1 through Step 8 can be isolated and purified by the per se known procedure, such as concentration, pH adjustment, redistribution, solvent extraction, column chromatography, crystallization, recrystallization, etc. However, the reaction mixture can be directly used in the next reaction step.

In connection with each of the above reactions for producing the compound (I) and the starting compounds or their salts, where the starting compound has an amino, carboxyl or hydroxyl group as the substituent, it can be used as previously protected with an appropriate protective group which is commonly used in peptide and other chemistry and, if necessary, the deprotected compound can be obtained by removing such protective group after the reaction.

The protective group for such amino group includes optionally substituted $C_{1-6}$ alkylcarbonyl groups (e.g. formyl, methylcabonyl, ethylcarbonyl, etc.), phenylcarbonyl, $C_{1-6}$ alkyloxycarbonyl groups (e.g. methoxycarbonyl, ethoxycarbonyl, etc.), phenyloxycarbonyl groups (e.g. benzoxycarbonyl etc.), $C_{7-10}$ aralkylcarbonyl groups (e.g. benzyloxycarbonyl etc.), trityl, phthaloyl and so on. These groups may be optionally substituted by 1 to 3 substituent groups such as, for example, halogen (e.g. fluoro, chloro, bromo, iodo), $C_{1-6}$ alkylcarbonyl groups (e.g. methylcarbonyl, ethylcarbonyl, butylcarbonyl, etc.) and nitro.

The protective group for said carboxyl group includes optionally substituted $C_{1-6}$ alkyl groups (e.g. methyl, ethyl, n-propyl, i-propyl, n-butyl, tert-butyl, etc.), phenyl, trityl, silyl and so on. The substituent may number 1 to about 3 and includes halogen (e.g. fluoro, chloro, bromo, iodo), $C_{1-6}$ alkylcarbonyl (e.g formyl, methylcarbonyl, ethylcarbonyl, butylcarbonyl, etc.) and nitro.

The protective group for said hydroxyl group includes optionally substituted $C_{1-6}$ alkyl groups (e.g. methyl, ethyl, n-propyl, i-propyl, n-butyl, tert-butyl, etc.), phenyl, $C_{7-10}$ aralkyl groups (e.g. benzyl etc.), $C_{1-6}$ alkylcarbonyl groups (e.g. formyl, methylcarbonyl, ethylcarbonyl, etc.), phenyloxycarbonyl groups (e.g. benzoxycarbonyl etc.), $C_{7-10}$ aralkylcarbonyl groups (e.g. benzyloxycarbonyl etc.), pyranyl, furanyl, silyl and so on. The substituent may number 1 to about 4 and includes halogen (e.g. fluoro, chloro, bromo, iodo), $C_{1-6}$ alkyl, phenyl, $C_{7-10}$ aralkyl, nitro and so on.

These protective groups can be removed by the per se known procedures or any procedures analogous thereto. For example, treatment with an acid or a base, reduction, irradiation with ultraviolet light, and treatment with hydrazine, phenylhydrazine, sodium N-methyldithiocarbamate, tetrabutylammonium fluoride or palladium acetate can be mentioned.

The compound (I) produced by the above methods can be isolated and purified by the routine procedures such as recrystallization, distillation and chromatography. When the compound (I) thus obtained is the free compound, it can be converted to a salt by the per se known procedure (e.g. neutralization) or any procedure analogous thereto. Conversely, when the product is a salt, it can be converted to the free compound or a different salt by the per se known procedure or any procedure analogous thereto.

When the compound (I) is an optically active compound, it can be resolved by the conventional optical resolution method to provide the d- and l-compounds.

The compound (I) and salts thereof according to the invention has excellent tachykinin receptor antagonizing activity, particularly potent antagonistic activity against substance P (hereinafter sometimes referred to briefly as SP), and is low in acute toxicity (Mice are dosed at 300 mg/kg p.o. and 100 mg/kg i.p. for observation of acute toxic symptoms or autonomic effects during the subsequent 72 hours; the response is no effect) and chronic toxicity, thus being a medicinally useful and safe substance.

Substance P (SP) is a neuropeptide discovered in an equine intestinal canal extract in 1931 and its structure, consisting of 11 amino acids, was established in 1971. SP is broadly distributed in the central and peripheral nervous systems and, in addition to being a primary sensory neurotransmitter, has various physiological activities such as vasodilating activity, smooth muscle contracting activity, neuronal excitatory activity, sialogogue activity and diuretic activity. It is known particularly that SP released by a pain impulse at the terminal of the cornu posterius of the spinal cord transmits pain information to secondary neurons and that SP released from the peripheral nerve terminal induces an inflammatory response in the nociceptive field. Moreover, SP is suspected to be involved in Alzheimer type dementia. Therefore, the compound (I) and ($I^a$) or salts thereof having potent SP receptor antagonizing activity are of value as a safe prophylactic/therapeutic drug for pain, inflammation, allergy and dementia in mammalian animals (e.g. mouse, rat, hamster, rabbit, cat, dog, bovine, sheep, monkey, man, etc.).

For medicinal use, the compound (I) or salts thereof of the invention can be formulated with suitable pharmacologically acceptable carriers or excipients (e.g. starch, lactose, sucrose, calcium carbonate, calcium phosphate, etc.), binders (e.g. starch, gum arabic, carboxymethylcellulose, hydroxypropylcellulose, crystalline cellulose, alginic acid, gelatin, polyvinylpyrrolidone, etc.), lubricants (e.g. stearic acid, magnesium stearate, calcium stearate, talc, etc.), disintegrators (e.g. carboxymethylcellulose calcium, talc, etc.) and diluents (e.g. physiological saline) and administered orally or otherwise in such dosage forms as powders, fine granules, granules, tablets, capsules, injections and so on. The dosage is dependent on the species of compound (I) or salts thereof, route of administration, disease condition, and patient's age and other background factors. However, for oral administration to an adult patient, for instance, a daily dose of about 0.005 to 50 mg, preferably about 0.05 to 10 mg, more preferably about 0.2 to 4 mg, per kg body weight is administered in 1 to 3 divided doses.

The following are the experimental data showing the pharmacological efficacy of the compound (I) or salts thereof of the present invention.

(1) Radioligand receptor binding inhibitory assay using receptor from rat forebrain The method of R. Qirion and C. Pilapil (Neuropeptide 4, 325 (1984)) was modified and used. The receptor was prepared from the brain of Wistar rats (male, 8 weeks old, Charles-River). The rat was sacrificed by decapitation and the forebrain was isolated. The forebrain was homogenized in 30 ml/rat of 150 mM Tris-HCl buffer (pH 7.4) containing 120 mM sodium chloride and 5 mM potassium chloride using a Polytron homogenizer (Kinematika, Germany) and centrifuged at 40,000×G for 20 minutes. The pellet was suspended in 30 ml of 50 mM Tris-HCl buffer (pH 7.4) containing 300 mM potassium chloride and 10 mM ethylenediaminetetracetic acid and stirred gently with ice-cooling for 30 minutes. This suspension was centrifuged at 40,000×G for 20 minutes and the pellet was washed with 30 ml of 50 mM Tris-HCl buffer (pH 7.4). The receptor specimen thus obtained was preserved frozen (−80° C.).

The above specimen was suspended in a reaction buffer (50 mM Tris-HCl buffer (pH 7.4), 0.02% bovine serum albumin, 1 mM phenylmethylsulfonyl fluoride, 2 μg/ml chymostatin, 40 μg/ml bacitracin, 3 mM manganese chloride) at a protein concentration of 1.5 mg/ml and a 100 μl portion of the suspension was used in the reaction. After addition of the sample and 125I-BHSP (0.46 KBq), the reaction was conducted in 0.2 ml of reaction buffer at 25° C. for 30 minutes. The amount of nonspecific binding was determined by adding substance P at a final concentration of $2\times10^{-6}$M. After the reaction, using a cell harvester (290PHD, Cambridge Technology, Inc., England), rapid filtration was carried out through a glass filter (GF/B, Whatman, U.S.A.) to stop the reaction. After washings three times with 250 μl of 50 mM Tris-HCl buffer (pH 7.4) containing 0.02% bovine serum albumin, the radioactivity remaining on the filter was measured with a gamma counter. Before use, the filter was immersed in 0.1% polyethyleneimine for 24 hours and air-dried.

The antagonistic activity of each test substance, in terms of the concentration necessary to cause 50% inhibition [$IC_{50}$] under the above conditions, was expressed in μM (Table 2).

TABLE 2

| Example Compound No. | $IC_{50}$ (μM) |
|---|---|
| 2 | 0.019 |
| 12 | 0.064 |
| 13 | 0.042 |
| 14 | 0.056 |
| 15 | 0.076 |
| 16 | 0.011 |
| 17 | 0.018 |
| 18 | 0.014 |
| 19 | 0.032 |
| 24 | 0.10 |

(2) Radioligand receptor binding inhibitory assay using receptor from human lymphoblast cells (IM-9)

The method of A. Margaret et al. [Molecular Pharmacology 42, 458 (1992)] was modified and used. The receptor was prepared from human lymphoblast cells (IM-9). IM-9 cells were grown in 175 cm² tissue culture flasks (100 ml×10) at a density approximately 2×10⁵/ml of RPMI 1640 with L-glutamine, 10% (V/V) heat inactivated fetal calf serum, penicillin (100 u/ml), and streptomycin (100 μg/ml) at 37° C. in 5%CO₂/95% air for 3 days. IM-9 cells were obtained by centrifugation at 500×g for 5 minutes at 5° C. The pellet obtained was washed once with phosphate buffer (Flow Laboratories, CAT. No. 28-103-05), homogenized using Polytron homogenizer(Kinematika, Germany) in 30 ml of 50 mM Tris-HCl buffer containing 120 mM NaCl, 5 mM KCl, 2 μg/ml phenylmethyl sufonyl fluoride, and 1 mM ethylenediamine tetra-acetic acid, and then centrifuged at 40,000×g for 20 minutes. The residue was washed twice with 30 ml of buffer described above, and preserved frozen (−80° C.).

The above specimen was suspended in a reaction buffer (50 mM Tris-HCl buffer (pH 7.4), 0.02% bovine serum albumin, 1 mM phenylmethylsulfonyl fluoride, 2 μg/ml chymostatin, 40 μg/ml bacitracin, 3 mM manganese chloride) at a protein concentration of 1.5 mg/ml and a 100 μl portion of the suspension was used in the reaction. After addition of the sample and 125I-BHSP (0.46 KBq), the reaction was conducted in 0.2 ml of reaction buffer at 25° C. for 30 minutes. The amount of nonspecific binding was determined by adding substance P at a final concentration of $2\times10^{-6}$M. After the reaction, using a cell harvester (290PHD, Cambridge Technology, Inc., England), rapid filtration was carried out through a glass filter (GF/B, Whatman, U.S.A.) to stop the reaction. After washing three times with 250 μl of 50 Tris-HCl buffer (pH 7.4) containing 0.02% bovine serum albumin, the radioactivity remaining on the filter was measured with a gamma counter. Before use, the filter was immersed in 0.1% polyethyleneimine for 24 hours and air-dried.

The antagonistic activity of each test substance, in terms of the concentration necessary to cause 50% inhibition [$IC_{50}$] under the above conditions, was expressed in μM (Table 3).

TABLE 3

| Example Compound No. | $IC_{50}$ (μM) |
|---|---|
| 1 | 0.016 |
| 3 | 0.023 |
| 42 | 0.076 |
| 52 | 0.0042 |
| 53 | 0.066 |

It is apparent from Table 2 and 3 that the compound (I) and salts thereof of the present invention have excellent substance P receptor antagonizing activity.

[Examples]

The following reference and working examples are further descriptive of the present invention. It should be understood that these are merely illustrative and by no means definitive of the invention and that many changes and modifications can be made within the scope of the invention.

In the following disclosure, "room temperature" means the range of 10° C. to 35° C.

In the presentation of NMR data, the following abbreviations were used. s, singlet; d, doublet; t, triplet; q, quartet; m, multiplet; b, broad; Hz, Herz.

Reference Example 1

2,6,7-Trimethyl-4-phenyl-1(2H)-isoquinolinone-3-carboxylic acid

Step 1

6,7-Dimethyl-4-phenylisocoumarin-3-carboxylic acid

A mixture of 2-benzoyl-4,5-dimethylbenzoic acid (11.4 g), acetone (300 ml), dimethylformamide (10 ml), potassium carbonate (6.83 g) and diethyl bromomalonate (12.84 g) was stirred at room temperature for 60 hours. The solvent was then distilled off and ethyl acetate was added to the residue.

The mixture was washed with water and dried (Na$_2$SO$_4$) and the solvent was distilled off. To the residue were added acetic acid (180 ml) and hydrochloric acid (180 ml) and the mixture was heated at 110° C. for 5 hours. The reaction mixture was then concentrated and the concentrate was diluted with water and extracted with ethyl acetate. The extract was washed with water and dried (Na$_2$SO$_4$) and the solvent was distilled off. The resulting crystals were recrystallized from ethyl acetate-isopropyl ether to provide the title compound. Melting point: 265°–268° C.

Step 2

4-Phenyl-2,6,7-trimethyl-1(2H)-isoquinolinone-3-carboxylic acid

To a solution of the compound obtained in Step 1 (3.75 g) in methanol (50 ml) was added 40% methylamine-methanol solution and the mixture was stirred at room temperature for 2 hours. The solvent was then distilled off and after addition of 4N-HCl-ethyl acetate (50 ml), the residue was stirred at room temperature for 2 hours. The solvent was then distilled off and water was added to the residue. The resulting crystals were recovered by filtration and washed with water, acetone and ethyl ether to provide the title compound as colorless crystals (3.51 g). Melting point: >300° C. (recrystallized from ethanol) NMR (200 MHz, CDCl$_3$+DMSO-d$_6$) ppm: 2.25 (3H, s), 2.39 (3H, s), 3.67 (3H, s), 6.91 (1H, s), 7.39–7.42 (5H, m), 8.24 (1H, s)

Elemental analysis for C$_{19}$H$_{17}$NO$_3$ Calcd.: C, 74.25; H, 5.58; N, 4.56 Found: C, 74.40; H, 5.50; N, 4.41

Using the compound obtained in Step 1 of Reference Example 1 and ethylamine, n-butylamine, N,N-dimethylaminoethylamine and ammonia, respectively, in lieu of methylamine, the procedure of Step 2 above was otherwise repeated to provide the compounds of Reference Examples 2 through 5, each as colorless crystals.

Reference Example 2

2-Ethyl-6,7-dimethyl-4-phenyl-1(2H)isoquinolinone-3-carboxylic acid

Melting point: 254°–256° C. (recrystallized from ethyl acetate-methanol)

Reference Example 3

2-n-Butyl-6,7-dimethyl-4-phenyl-1(2H)isoquinolinone-3-carboxylic acid

Melting point: 218°–219° C. (recrystallized from ethylacetate-isopropyl ether)

Reference Example 4

2-(2-Diethylaminoethyl)-6,7-dimethyl-4-phenyl-1(2H)-isoquinolinone-3-carboxylic acid Melting point: 291°–293° C. (recrystallized from chloroform-methanol)

Reference Example 5

6,7-Dimethyl-4-phenyl-1(2H)-isoquinolinone-3-carboxylic acid

Melting point: 325°–327° C. (recrystallized from chloroform-methanol)

Reference Example 6

4-(4-Fluorophenyl)-2,6,7-trimethyl-1(2H)-isoquinolinone-3-carboxylic acid

Using 4,5-dimethyl-2-(4-fluorobenzoyl)benzoic acid in lieu of 2-benzoyl-4,5-dimethylbenzoic acid, the procedure of Step 1 of Reference Example 1 was otherwise repeated to provide 4-(2-fluorophenyl)-6,7-dimethylisocoumarin-3-carboxylic acid [m.p. 214°–217° C. (recrystallized from ethyl acetate)]. This compound was subjected to the same reaction as Step 2 of Reference Example 1 to provide the title compound as colorless crystals.

Melting point: 309°–312° C. (recrystallized from chloroform-methanol)

Reference Example 7

5-Fluoro-4-(4-fluorophenyl)-2-methyl-1(2H)isoquinolinone-3-carboxylic acid

Using 5-fluoro-4-(4-fluorophenyl)isocoumarin-3-carboxylic acid and methylamine, the procedure of Step 2 of Reference Example 1 was carried out to provide the title compound as colorless crystals.

Melting point: 256°–257° C. (recrystallized from acetone-isopropyl ether)

Reference Example 8

6,7-Dichloro-2-methyl-4-phenyl-1(2H)isoquinolinone-3-carboxylic acid

Using 2-benzoyl-4,5-dichlorobenzoic acid in lieu of 2-benzoyl-4,5-dimethylbenzoic acid, the procedure of Step 1 of Reference Example 1 was otherwise repeated to provide 6,7-dichloro-4-phenylisocoumarin-3-carboxylic acid [m.p. 243°–244° C. (recrystallized from ethyl acetate-isopropyl ether)]. This compound was reacted and treated in the same manner as in Step 2 of Reference Example 1 to provide the title compound as colorless crystals.

Melting point: >300° C. (recrystallized from chloroform-methanol

Reference Example 9

2,6,7-Trimethyl-4-(2-methylphenyl)-1(2H)isoquinolinone-3-carboxyllic acid

Step 1

4,5-Dimethyl-2-(2-methylbenzoyl)benzoic acid N-cyanomethyl-N-methylamide

A mixture of 4,5-dimethyl-2-(2methylbenzoyl)benzoic acid (7.7 g), dichloromethane(100ml), oxalyl chloride(2.74 ml) and N,N-dimethylformamide (3 drops) was stirred at room temperature for 2 hours. The solvent was evaporated, and the residue was dissolved in dichloromethane(50 ml). The solution was added dropwise to a mixture of N-methylaminoacetonitrile hydrochloride(4.86 g), triethylamine(12.0 ml), and dichloromethane(70 ml) with stirring and ice-cooling. The mixture was stirred at room temperature for 12 hours. The solvent was evaporated, and to the residue was added ethyl acetate. The mixture was washed successively with water, dil.HCl, aq.NaHCO$_3$, and water, and dried(MgSO4). The solvent was evaporated to provide the title compound as a colorless oil (9.2 g).

NMR (200 MHz, CDCl$_3$)ppm: 2.26 (3H, s), 2.35 (3H, s), 2.37 (3H, s), 2.99 (3H, s), 4.47 (2H, s), 7.05–7.40 (6H, m)

Step 2

3-Cyano-2,6,7-trimethyl-4-(2-methylphenyl)-1(2H)isoquinolinone

A mixture of the compound obtained in Step 1(9.1 g), toluene(200 ml), and 1,8-diazabicyclo[5.4.0)-7-undecene(8 ml) was stirred under refrux for 7 hours. Ethyl acetate was added to the mixture, which was washed successively with water, dil.HCl, aq. NaCHO$_3$, and water, and dried(MgSO$_4$). The solvent was evaporated to provide the title compound as colorless crystals(6.3 g).

Melting point: 217°–218° C. (recrystallized from ethyl acetate)

Step 3

2,6,7-Trimethyl-4-(2-methylphenyl)-1(2H)isoquinolinone-3-carboxylic acid amide

A mixture of the compound obtained in Step 2(5.8 g), ethanol(20 ml), and 1N-NaOH(25 ml) was stirred under refrux for 3 hours. The mixture was concentrated, and to the concentrate was added dil.HCl. The crystals separated were collected by filtration, and washed successively with water acetone, and ethyl ether to provide the title compound as colorless crystals (6.1 g).

Melting point: 296°–299° C. (recrystallized from methanol)

Step 4

2,6,7-Trimethyl-4-(2-methylphenyl)-1(2H)isoquinolinone-3-carboxyllic acid

To a mixture of the compound obtained in Step 3(1.0 g), acetic acid(15 ml), and conc.HCl(30 ml) was added portionwise sodium nitrite(6.2 g) with stirring, and the mixture was stirred at room temperature for 5 hours. Water was added to the mixture. The crystals separated were collected by filtration, and washed succesively with water, acetone, and ethyl ether to provide the title compound as colorless crystals (0.97 g).

Melting point: 291°–292.5° C. (recrystallized from ethyl acetate)

Using 2-benzoyl benzoic acids having various substituents in lieu of 4,5-dimethyl-2-(2-methylbenzoyl)benzoic acid used in Reference 9, Step 1, the same reactions as Step 2 through 4 were carried out to provide the compound of Reference Example 10 to 15 as colorless crystals.

Reference Example 10

4-(2,6-dimethylphenyl)-2-methyl-1(2H)isoquinolinone-3-carboxylic acid

Melting point: 284°–285.5° C. (recrystallization from methanol-ethanol)

Reference Example 11

4-(4-Fluoro-2-methylphenyl)-2-methyl-1(2H)isoquinolinone-3-carboxylic acid

Melting point: 257.5°–260° C. (recrystallization from ethyl acetate-ethanol)

Reference Example 12

2-methyl-4-(2-methylphenyl)-1(2H)-isoquinolinone-3-carboxylic acid

Melting point: 225°–227° C. (recrystallization from ethyl acetate-ethanol)

Reference Example 13

4-(2-ethylphenyl)-2-methyl-1(2H)-isoquinolinone-3-carboxylic acid

Melting point: 100°–102° C. (recrystallization from ethyl acetate-isopropyl ether)

Reference Example 14

4-(2-ethylphenyl)-2,6,7-trimethyl-1(2H)isoquinolinone-3-carboxylic acid

Melting point: 214°–215° C. (recrystallization from ethyl-ethanol)

Reference Example 15

4-(2,6-dimethylphenyl)-2,6,7-trimethyl-1(2H)isoquinolinone-3-carboxylic acid

Melting point: >300° C. (recrystallization from ethyl acetate-ethanol)

Example 1

N-Benzyl-N'-(1,2-dihydro-2,6,7-trimethyl-1-oxo-4-phenylisoquinolin-3-yl)-N-methylurea To a mixture of 4-phenyl-2,6,7-trimethyl-1(2H)isoquinolinone-3-carboxylic acid (307 mg), diphenylphosphorylazide (DPPA) (0.290 ml) and benzene (20 ml) was added triethylamine (0.142 ml) dropwise at room temperature with constant stirring. This mixture was further stirred at room temperature for 1 hour and then under reflux for 30 minutes. Then, N-methylbenzylamine (0.154 ml) was added and the mixture was refluxed for 30 minutes. The reaction mixture was diluted with ethyl acetate, washed with water, diluted hydrochloric acid, aqueous sodium hydrogen carbonate solution and water in that order and dried ($Na_2SO_4$). Finally the solvent was distilled off to provide the title compound as colorless crystals (250 mg).

Melting point: 174°–176° C. (recrystallized from acetone-ethylether)

NMR (200 MHz, $CDCl_3$) ppm: 2.23 (3H, s), 2.37 (3H, s), 2.65 (3H, s), 3.65 (3H, s), 4.39 (2H, b), 5.70 (1H, s), 6.85 (1H, s), 7.0–7.5 (10H, m), 8.23 (1H, s)

Elemental analysis for $C_{27}H_{27}N_3O_2$ Calcd.: C, 76.21; H, 6.40; N, 9.87 Found: C, 75.88; H, 6.53; N, 9.66

Examples 2–74

In the same manner as Example 1, 1(2H)-isoquinolinone-3-carboxylic acid compounds having various substituents were treated with DPPA and triethylamine in benzene and, then, reacted with amines having various substituents to provide the corresponding compounds of Examples 2–74.

Example 2

N-Benzyl-N'-(1,2-dihydro-2,6,7-trimethyl-1-oxo-4-phenylisoquinolin-3-yl)urea

Melting point: 234°–236° C. (recrystallized from tetrahydrofuran)

NMR (200 MHz, $CDCl_3$) ppm: 2.21 (3H, s), 2.33 (3H, s), 3.61 (3H, s), 4.33 (2H, bs), 5.1 (1H, b), 5.89 (1H, s), 6.86 (1H, s), 7.1–7.4 (10H, m), 8.14 (1H, s)

Elemental analysis for $C_{26}H_{25}N_3O_2$ Calcd.: C, 75.89; H, 6.12; N, 10.21 Found: C, 75.76; H, 6.12; N, 10.13

Example 3

N-(1,2-Dihydro-2,6,7-trimethyl-1-oxo-4-phenylisoquinolin-3-yl)-N'-(2-methoxybenzyl)-N'-methylurea Melting point: 270°–272° C. (recrystallized from ethyl acetate-ethyl ether)

NMR (200 MHz, $CDCl_3$) ppm: 2.23 (3H, s), 2.37 (3H, s), 2.81 (3H, s), 3.62 (3H, s), 3.74 (3H, s), 4.28 (2H, s), 6.07 (1H, s), 6.80–7.41 (10H, m), 8.23 (1H, s)

Elemental analysis for $C_{28}H_{29}N_3O_3$ Calcd.: C, 73.82; H, 6.42; N, 9.22 Found: C, 73.57; H, 6.43; N, 9.13

Example 4

N-(1,2-Dihydro-2,6,7-trimethyl-1-oxo-4-phenylisoquinolin-3-yl)-N'-(2-methoxybenzyl)urea Melting point: 225 (partial decompn.) –270° C. (recrystallized from tetrahydrofuran-methanol)

NMR (200 MHz, CDCl$_3$) ppm: 2.23 (3H, s), 2.37 (3H, s), 3.54 (3H, s), 3.68 (3H, s), 4.30 (2H, s), 5.27 (1H, b), 5.95 (1H, s), 6.8–7.4 (10H, m), 8.21 (1H, s)

Elemental analysis for C$_{27}$H$_{27}$N$_3$O$_3$•0.2H$_2$O Calcd.: C, 72.85; H, 6.21; N, 9.48 Found: C, 72.75; H, 6.14; N, 9.38

Example 5

N-(1,2-Dihydro-2,6,7-trimethyl-1-oxo-4-phenylisoquinolin-3-yl)-N'-methyl-N'-phenethylurea Melting point: 184°–188° C. (recrystallized from ethyl acetate-ethyl ether)

NMR (200 MHz, CDCl$_3$) ppm: 2.23 (3H, s), 2.37 (3H, s), 2.59 (3H, s), 2.6 (2H, m), 3.56 (2H, m), 3.54 (3H, s), 5.58 (1H, s), 6.85 (1H, s), 7.1–7.5 (10H, m), 8.23 (1H, s)

Elemental analysis for C$_{28}$H$_{29}$N$_3$O$_2$ Calcd.: C, 76.51; H, 6.65; N, 9.56 Found: C, 76.67; H, 6.69; N, 9.42

Example 6

2,6,7-Trimethyl-4-phenyl-3-(4-phenylpiperidinocarbonyl)amino-1(2H)-isoquinolinone Melting point: 240°–242° C. (recrystallized from acetone)

Elemental analysis for C$_{30}$H$_{31}$N$_3$O$_2$ Calcd.: C, 77.39; H, 6.71; N, 9.03 Found: C, 77.10; H, 6.70; N, 9.00

Example 7

2,6,7-Trimethyl-4-phenyl-3-(4-phenylpiperazinocarbonyl)amino-1(2H)-isoquinolinone Melting point: 238°–241° C. (recrystallized from acetone-ethylacetate)

Elemental analysis for C$_{29}$H$_{30}$N$_4$O$_2$•0.2H$_2$O Calcd.: C, 74.08; H, 6.52; N, 11.92 Found: C, 74.05; H, 6.44; N, 11.92

Example 8

3-(4-Benzylpiperazinocarbonyl)amino-2,6,7-trimethyl-4-phenyl-1(2H)-isoquinolinone Melting point: 233°–236° C. (recrystallized from methanol)

NMR (200 MHz, CDCl$_3$) ppm: 2.23 (3H, s), 2.26 (4H, b), 2.37 (3H, s), 3.22 (4H, b), 3.46 (2H, s), 3.60 (3H, s), 5.72 (1H, s), 6.86 (1H, s), 7.30–7.48 (10H, m), 8.22 (1H, s)

Elemental analysis for C$_{30}$H$_{32}$N$_4$O$_2$ Calcd.: C, 74.97; H, 6.71; N, 11.66 Found: C, 75.18; H, 6.69; N, 11.66

Example 9

N-(1,2-Dihydro-2,6,7-trimethyl-1-oxo-4-phenylisoquinolin-3-yl)-N'-methyl-N'-phenylurea Melting point 168°–170° C. (recrystallized from ethyl acetate-ethyl ether)

Elemental analysis for C$_{26}$H$_{25}$N$_3$O$_2$ Calcd.: C, 75.89; H, 6.12; N, 10.21 Found: C, 75.54; H, 6.21; N, 10.00

Example 10

N-Benzyl-N'-[4-(4-fluorophenyl)-1,2-dihydro-2,6,7-trimethyl-1-oxo-isoquinolin-3-yl]-urea Melting point: 250°–253° C. (recrystallized from ethyl acetate-methanol)

NMR (200 MHz, CDCl$_3$+DMSO-d$_6$) ppm: 2.25 (3H, s), 2.37 (3H, s), 3.64 (3H, s), 4.33 (2H, bs), 6.86 (1H, s), 7.03–7.35 (9H, m), 8.20 (1H, s)

Elemental analysis for CH$_{26}$H$_{24}$N$_3$O$_2$F•0.25H$_2$O Calcd.: C, 71.96; H, 5.69; N, 9.68 Found: C, 71.90; H, 5.64; N, 9.66

Example 11

N-[4-(4-Fluorophenyl)-1,2-dihydro-2,6,7-trimethyl-1-oxo-isoquinolin-3-yl]-N'-(2-methoxybenzyl)urea Melting point: 190°–191° C. (recrystallized from ethyl acetate-ethyl ether)

NMR (200 MHz, CDCl$_3$) ppm: 2.23 (3H, s), 2.37 (3H, s), 2.90 (3H, s), 3.60 (3H, s), 3.76 (3H, s), 4.31 (2H, s), 6.06 (1H, s), 6.81 (1H, s), 6.85–7.30 (9H, m), 8.22 (1H, s)

Elemental analysis for C$_{28}$H$_{28}$N$_3$O$_3$F Calcd.: C, 71.02; H, 5.96; N, 8.87 Found: C, 70.90; H, 6.01; N, 8.67

Example 12

N-(2-Furfuryl)-N'-(1,2-dihydro-2,6,7-trimethyl-1-oxo-4-phenylisoquinolin-3-yl)urea Melting point: 240° C. (coloration), 257°–258° C. (recrystallized from tetrahydrofuran-methanol)

NMR (200 MHz, CDCl$_3$) ppm: 2.24 (3H, s), 2.37 (3H, s), 3.61 (3H, s), 4.31 (2H, s), 6.14 (1H, d, J=2.4 Hz), 6.3 (1H, b), 6.33 (1H, m), 6.91 (1H, s), 7.24–7.42 (6H, m), 8.19 (1H, s)

Elemental analysis for C$_{24}$H$_{23}$N$_3$O$_3$ Calcd.: C, 71.80; H, 5.77; N, 10.47 Found: C, 71.61; H, 5.78; N, 10.29

Example 13

N-(1,2-Dihydro-2,6,7-trimethyl-1-oxo-4-phenylisoquinolin-3-yl)-N'-(2-pyridinemethyl)urea Melting point: 221°–222° C. (recrystallized from tetrahydrofuran)

NMR (200 MHz, CDCl$_3$) ppm: 2.23 (3H, s), 2.37 (3H, s), 3.60 (3H, s), 4.50 (2H, d, J=5.8 Hz), 6.35 (1H, b), 6.88 (1H, s), 7.2–7.4 (7H, m), 7.90 (1H, m), 8.23 (1H, s), 8.46 (1H, m)

Elemental analysis for C$_{25}$H$_{24}$N$_4$O$_2$•0.3H$_2$O Calcd.: C, 71.85; H, 5.93; N, 13.41 Found: C, 71.89; H, 5.80; N, 13.13

Example 14

N-(1,2-Dihydro-2,6,7-trimethyl-1-oxo-4-Phenylisoquinolin-3-yl)-N'-(2-thiophenemethyl)urea Melting point: 236°–239° C. (recrystallized from tetrahydro furan)

NMR (200 MHz, CDCl$_3$) ppm: 2.24 (3H, s), 3.63 (3H, s), 4.49 (2H, bs), 6.35 (1H, b), 6.89–7.42 (9H, m), 8.19 (1H, s)

Elemental analysis for C$_{24}$H$_{23}$N$_3$O$_2$S Calcd.: C, 69.04; H, 5.55; N, 10.06 Found: C, 68.83; H, 5.49; N, 10.04

Example 15

N-Cyclohexylmethyl-N'-(1,2-dihydro-2,6,7-trimethyl-1-oxo-4-phenylisoquinolin-3-yl)urea Melting point 224°–227° C. (recrystallized from tetrahydro furan-ethyl acetate)

NMR (200 MHz, CDCl$_3$) ppm: 0.70–0.95 (2H, m), 1.05–1.40 (4H, m), 1.50–1.80 (5H, m), 2.23 (3H, s), 2.34 (3H, s), 2.94 (2H, t, J=6 Hz), 3.58 (3H, s), 4.96 (1H, t, J=6 Hz), 6.17 (1H, s), 6.89 (1H, s), 7.20–7.35 (2H, m), 7.35–7.55 (3H, m), 8.14 (1H, s)

Elemental analysis for $C_{26}H_{31}N_3O_2$ Calcd.: C, 74.79; H, 7.48; N, 10.06 Found: C, 74.61; H, 7.44; N, 9.99

Example 16

N-(1,2-Dihydro-2,6,7-trimethyl-1-oxo-4-phenylisoquinolin-3-yl)-N'-(4-methylbenzyl)urea Melting point: 214°–216° C. (recrystallized from tetrahydro furan-isopropyl ether)

NMR (200 MHz, DMSO-$d_6$) ppm: 2.21 (3H, s), 2.29 (3H, s), 2.35 (3H, s), 3.45 (3H, s), 4.14 (2H, bs), 6.73 (1H, m), 6.85 (1H, s), 6.99 (2H, d, J=8 Hz), 7.11 (2H, d, J=8 Hz), 7.25 (2H, m), 7.45 (3H, m), 7.84 (1H, s), 8.07 (1H, s)

Elemental analysis for $C_{27}H_{27}N_3O_2$ Calcd.: C, 76.21; H, 6.40; N, 9.87 Found: C, 76.40; H, 6.52; N, 9.75

Example 17

N-(1,2-Dihydro-2,6,7-trimethyl-1-oxo-4-phenylisoquinolin-3-yl)-N'-(3-methylbenzyl)urea Melting point: 230°–233° C. (recrystallized from tetrahydrofuran-isopropyl ether)

NMR (200 MHz, DMSO-$d_6$) ppm: 2.21 (3H, s), 2.29 (3H, s), 2.35 (3H, s), 3.46 (3H, s), 4.15 (2H, bs), 6.76 (1H, m), 6.85 (1H, s), 6.80–7.55 (9H, m), 7.85 (1H, s), 8.07 (1H, s)

Elemental analysis for $C_{27}H_2N_3O_2$ Calcd.: C, 76.21; H, 6.40; N, 9.87 Found: C, 76.00; H, 6.50; N, 9.61

Example 18

N-(1,2-Dihydro-2,6,7-trimethyl-1-oxo-4-phenylisoquinolin-3-yl)-N'-(2-methylbenzyl)urea Melting point: 238°–241° C. (recrystallized from chloroform-methanol)

NMR (200 MHz, DMSO-$d_6$) ppm: 2.14 (6H, s), 2.35 (3H, s), 3.46 (3H, s), 4.15 (2H, bs), 6.64 (1H, m), 6.85 (1H, s), 6.99 (1H, m), 7.12 (3H, m), 7.25 (2H, m), 7.45 (3H, m), 7.82 (1H, s), 8.07 (1H, s)

Elemental analysis for $C_{27}H_{27}N_3O_2$ Calcd.: C, 76.21; H, 6.40; N, 9.87 Found: C, 76.01; H, 6.65; N, 9.65

Example 19

N-Benzyl-N'-(2-ethyl-1,2-dihydro-6,7-dimethyl-1-oxo-4-phenylisoquinolin-3-yl)urea Melting point: 162.5°–164.5° C. (recrystallized from ethyl acetate-methanol)

NMR (200 MHz, CDCl$_3$+DMSO-$d_6$) ppm: 1.33 (3H, t, J=7 Hz), 2.23 (3H, s), 2.37 (3H, s), 4.03–4.40 (2H, m), 4.30 (2H, bs), 6.89 (1H, s), 7.03–7.46 (10H, m), 8.22 (1H, s)

Elemental analysis for $C_{27}H_{27}N_3O_2$ Calcd.: C, 76.21; H, 6.40; N, 9.87 Found: C, 75.93; H, 6.41; N, 9.75

Example 20

N-Benzyl-N'-(1,2-dihydro-6,7-dimethyl-1-oxo-4-phenylisoquinolin-3-yl)urea

Melting point: 235°–237° C. (recrystallized from acetone-ethyl ether)

NMR (200 MHz, CDCl$_3$) ppm: 2.21 (3H, s), 2.33 (3H, s), 4.28 (2H, s), 5.50 (1H, b), 6.65 (1H, b), 6.74 (1H, s), 7.20–7.55 (10H, m), 8.10 (1H, s)

Elemental analysis for $C_{25}H_{23}N_3O_2$ Calcd.: C, 75.55; H, 5.83; N, 10.57 Found: C, 75.23; H, 5.81; N, 10.47

Example 21

N-Benzyl-N'-(1,2-dihydro-6,7-dimethyl-1-oxo-4-phenylisoquinolin-3-yl)-N-methylurea Melting point: 176°–177° C. (recrystallized from acetone-ethyl ether)

NMR (200 MHz, CDCl$_3$) ppm: 2.22 (3H, s), 2.34 (3H, s), 2.75 (3H, s), 4.33 (2H, s), 6.52 (1H, s), 6.76 (1H, s), 7.01–7.47 (10H, m), 8.15 (1H, s)

Elemental analysis for $C_{26}H_{25}N_3O_2$ Calcd.: C, 75.89; H, 6.12; N, 10.21 Found: C, 75.71; H, 6.12; N, 10.19

Example 22

N-Benzyl-N'-[4-(4-fluorophenyl)-1,2-dihydro-2-methyl-1-oxoisoquinolin-3-yl]urea

Melting point: 219°–220° C. (recrystallized from ethyl acetate-methanol)

NMR (200 MHz, CDCl$_3$+DMSO-$d_6$) ppm: 3.66 (3H, s), 4.33 (2H, bs), 7.03–7.39 (9H, m), 7.39–7.57 (3H, m), 8.45 (1H, d, J=7.8 Hz)

Elemental analysis for $C_{24}H_{20}N_3O_2F$ Calcd.: C, 71.81;.H, 5.02; N, 10.47 Found: C, 71.57; H, 5.04; N, 10.48

Example 23

N-Benzyl-N'-(6-chloro-1,2-dihydro-2-methyl-1-oxo-4-phenylisoquinolin-3-yl)urea

Melting point: 219°–220° C. (recrystallized from ethyl acetate-methanol)

NMR (200 MHz, CDCl$_3$+DMSO-$d_6$) ppm: 3.65 (3H, s), 4.33 (2H, bs), 7.08–7.48 (12H, m), 8.38 (1H, d, J=8.6 Hz)

Elemental analysis for $C_{24}H_{20}N_3O_2Cl$ Calcd.: C, 68.98; H, 4.82; N, 10.06 Found: C, 68.64; H, 4.86; N, 9.98

Example 24

N-Benzyl-N'-[1,2-dihydro-4-(2-methoxyphenyl)-2-methyl-1-oxoisoquinolin-3-yl]urea Melting point: 219°–221° C. (recrystallized from ethyl acetate-methanol)

NMR (200 MHz, CDCl$_3$+DMSO-$d_6$) ppm: 3.60 (3H, s), 3.67 (3H, s), 4.30 (2H, dd, J=15.4, 31.6 Hz), 6.82–7.55 (12H, m), 8.45 (1H, d, J=7.2 Hz)

Elemental analysis for $C_{25}H_{23}N_3O_3$ Calcd.: C, 72.62; H, 5.61; N, 10.16 Found: C, 72.39; H, 5.66; N, 10.16

Example 25

N-Benzyl-N'-[5-fluoro-4-(4-fluorophenyl)-1,2-dihydro-2-methyl-1-oxoisoquinolin-3-yl]urea Melting point: 214°–216° C. (recrystallized from ethyl acetate-methanol)

NMR (200 MHz, CDCl$_3$+DMSO-d) ppm: 3.64 (3H, s), 4.32 (2H, bs), 6.97–7.44 (1H, m), 8.29 (1H, d, J=8.0 Hz)

Elemental analysis for $C_{24}H_{19}N_3O_2F_2$ Calcd.: C, 68.73; H, 4.57; N, 10.02 Found: C, 68.60; H, 4.56; N, 9.99

Example 26

N-(1,2-Dihydro-2,6,7-trimethyl-1-oxo-4-phenylisoquinolin-3-yl)-N'-(3-methylphenyl)urea Melting point: >300° C. (recrystallized from ethanol)

NMR (200 MHz, CDCl$_3$+DMSO-d6) ppm: 2.24 (3H, s ), 2.30 (3H, s), 2.37 (3H, s), 3.65 (3H, s), 6.82 (1H, d, J=6.8 Hz), 6.91 (1H, s), 7.00–7.17 (2H, m) , 7.21 (1H, bs), 7.26–7.53 (6H, m), 8.07 (1H, bs), 8.20 (1H, s)

Elemental analysis for C$_{26}$H$_{25}$N$_3$O$_2$ Calcd.: C, 75.89; H, 6.12; N, 10.21 Found: C, 75.65; H, 6.28; N, 10.13

Example 27

N-(2,4-Difluorophenyl)-N'-(1,2-dihydro-2,6,7-trimethyl-1-oxo-4-phenylinolin-3-yl)urea Melting point: >300° C. (recrystallized from ethanol)

NMR (200 MHz, CDCl$_3$+DMSO-d$_6$) ppm: 2.24 (3H, s), 2.38 (3H, s), 3.66 (3H, s), 6.72–6.89 (2H, m), 6.91 (1H, s), 7.27–7.55 (5H, m), 7.89 (1H, bs), 8.05–8.30 (2H, m), 8.22 (1H, s)

Elemental analysis for C$_{25}$H$_{21}$N$_3$O$_2$F$_2$ Calcd.: C, 69.27; H, 4.88; N, 9.69 Found: C, 69.36; H, 4.92; N, 9.34

Example 28

N-(2-Ethyl-1,2-dihydro-6,7-dimethyl-1-oxo-4-phenylisoquinolin-3-yl)-N'-(3-methylphenyl)urea Melting point: 237°–240° C. (recrystallized from acetone-tetrahydrofuran)

Elemental analysis for C$_{27}$H$_{27}$N$_3$O$_2$ Calcd.: C, 76.21; H, 6.40; N, 9.87 Found: C, 75.95; H, 6.47; N, 9.57

Example 29

N-(2-n-Butyl-1,2-dihydro-6,7-dimethyl-1-oxo-4-phenylisoquinolin-3-yl)-N'-(3-methylphenyl)urea Melting point: 222°–223° C. (recrystallized from ethyl acetate-isopropyl ether)

NMR (200 MHz, CDCl$_3$) ppm: 0.85 (3H, t, J=7.2 Hz), 1.22–1.45 (2H, m), 1.53–1.80 (2H, m), 2.22 (3H, s), 2.25 (3H, s), 2.30 (3H, s), 3.95–4.40 (2H, m), 6.67 (1H, bs), 6.77–6.97 (4H, m), 7.02–7.18 (2H, m), 7.20–7.55 (5H, m), 8.11 (1H, s)

Elemental analysis for C$_{29}$H$_{31}$N$_3$O$_2$•0.3 H$_2$O Calcd.: C, 75.89; H, 6.94; N, 9.15 Found: C, 75.87; H, 6.92; N, 8.86

Example 30

N-[2-(2-Diethylaminoethyl)-1,2-dihydro-6,7-di-methyl-1-oxo-4-phenylisoquinolin-3-yl]-N'-(3-methylphenyl)urea Melting point: 220°–222° C. (recrystallized from chloroform-methanol)

Example 31

N-[4-(4-Fluorophenyl)-1,2-dihydro-2,6,7-trimethyl-1-oxoisoquinolin-3-yl]-N'-(3-methylphenyl)urea Melting point: 320°–325° C. (decompn.) (recrystallized from acetone)

Elemental analysis for C$_{26}$H$_{24}$N$_3$O$_2$F Calcd.: C, 72.71; H, 5.63; N, 9.78 Found: C, 72.34; H, 5.62; N, 9.58

Example 32

N-(1,2-Dihydro-2,6,7-trimethyl-1-oxo-4-phenylisoquinolin-3-yl)-N'-(3-isopropoxyphenyl)urea Melting point: >300° C. (recrystallized from ethanol)

NMR (200 MHz, CDCl$_3$) ppm: 1.31 (6H, d, J=6 Hz), 2.24 (3H, s), 2.37 (3H, s), 3.65 (3H, s), 4.56 (1H, q, J=6 Hz), 6.53 (1H, dd, J=8.0, 1.8 Hz), 6.73 (1H, dd, J=8.0, 1.4 Hz), 6.91 (1H, s), 7.02–7.65 (8H, m), 8.20 (2H, s)

Elemental analysis for C$_{28}$H$_{29}$N$_3$O$_3$ Calcd.: C, 73.82; H, 6.42; N, 9.22 Found: C, 73.77; H, 6.47; N, 9.47

Example 33

N-(1,2-Dihydro-2,6,7-trimethyl-1-oxo-4-phenylisoquinolin-3-yl)-N'-(2-thiazolyl)urea Melting point: >300° C. (recrystallized from ethanol)

NMR (200 MHz, CDCl$_3$) ppm: 2.25 (3H, s), 2.38 (3H, s), 3.65 (3H, s), 6.75–6.93 (1H, m), 6.90 (1H, s), 7.13–7.60 (6H, m), 8.22 (1H, s)

Elemental analysis for C$_{22}$H$_{20}$N$_4$O$_2$S•0.5 EtOH Calcd.: C, 64.62; H, 5.42; N, 13.10 Found: C, 64.94; H, 5.29; N, 12.92

Example 34

N-(1,2-Dihydro-2,6,7-trimethyl-1-oxo-4-phenylisoquinolin-3-yl)-N'-[2-(4-methylthiazolyl]urea Melting point: 268°–271° C. (recrystallized from tetrahydrofuran)

Elemental analysis for C$_{23}$H$_{22}$N$_4$O$_2$S Calcd.: C, 66.01; H, 5.30; N, 13.39 Found: C, 65.82; H, 5.29; N, 13.34

Example 35

N-(1,2-Dihydro-2,6,7-trimethyl-1-oxo-4-phenylisoquinolin-3-yl)-N'-[2-(5-methyl-1,3,4-thiadiazolyl)]urea Melting point: 310°–315° C. (recrystallized from methanolchloroform)

Elemental analysis for C$_{22}$H$_{21}$N$_5$O$_2$S•0.25 H$_2$O Calcd.: C, 62.32; H, 5.11; N, 16.52 Found: C, 62.27; H, 4.96; N, 16.52

Example 36

N-[2-(5-Cyclopropyl-1,3,4-thiadiazolyl)-N'-(1,2-dihydro-2,6,7-trimethyl-1-oxo-4-phenylisoquinolin-3-yl)urea Melting point: 183°–188° C. (recrystallized from tetrahydrofuran)

Elemental analysis for C$_{24}$H$_{23}$N$_5$O$_2$S•0.5 H$_2$O Calcd.: C, 63.41; H, 5.32; N, 15.40 Found: C, 63.52; H, 5.09; N, 15.40

Example 37

N-(6,7-Dichloro-1,2-dihydro-2-methyl-1-oxo-4-phenylisoquinolin-3-yl)-N'-(3-methylphenyl)urea Melting point: >300° C. (recrystallized from chloroform-methanol)

NMR (200 MHz, CDCl$_3$) ppm: 2.31 (3H, s), 3.67 (3H, s), 6.84 (1H, d, J=7.6 Hz), 7.00–7.64 (10H, m), 8.19 (1H, bs), 8.53 (1H, s)

Elemental analysis for C$_{24}$H$_{19}$N$_3$O$_2$Cl$_2$•H$_2$O Calcd.: C, 61.29; H, 4.50; N, 8.93 Found: C, 61.46; H, 4.29; N, 8.77

Example 38

N-(1,2-Dihydro-2,6,7-trimethyl-1-oxo-4-phenylisoquinolin-3-yl)-N'-(4-methoxybenzyl)urea Melting point: 210°–211° C. (recrystallized from tetrahydrofuran-isopropyl ether)

NMR (200 MHz, CDCl$_3$) ppm: 2.17 (3H,s), 2.24 (3H, s), 3.50 (3H,s), 3.77(3H, s), 4.17 (2H, bs), 5.57 (1H, bs), 6.37 (1H, s), 6.78 (2H, d, J=8.8 Hz) , 6.80 (1H,s), 7.04 (2H, d, J=8.8 Hz), 7.05–7.20 (2H, m), 7.30–7.40 (2H, m), 7.96 (1H, s)

Example 39

N-(1,2-Dihydro-2,6,7-trimethyl-1-oxo-4-phenylisoquinolin-3-yl)-N'-(3-methoxybenzyl)urea Melting point: 221.5°–222.57° C. (recrystallized from tetrahydrofuran-isopropyl ether)

NMR (200 MHz, CDCl$_3$) ppm: 2.22 (3H, s), 2.35 (3H, s), 3.62 (3H, s), 3.79 (3H, s), 4.29 (2H, bs), 6.10 (1H, bm), 6.70–6.85 (3H, m), 6.89 (1H, s), 7.05 (1H, s), 7.15–7.45 (6H, m), 8.17 (1H, s)

Elemental analysis for C$_{27}$H$_{27}$N$_3$O$_2$ Calcd.: C, 73.45; H, 6.16; N, 9.52 Found: C, 73.32; H, 6.12; N, 9.35

Example 40

N-(4-Chlorobenzyl)-N'-(1,2-dihydro-2,6,7-trimethyl-1-oxo-4-phenylisoquinolin-3-yl)urea Melting point: about 245° C. (decomp.) (recrystallized from tetrahydrofuran-isopropyl ether)

NMR (200 MHz, CDCl$_3$) ppm: 2.22 (3H, s), 2.34 (3H, s), 3.60 (3H, s), 4.26 (2H, bs), 6.18 (1H, bm), 6.87 (1H, s), 7.00–7.45 (10H, m), 8.14 (1H, s)

Elemental analysis for C$_{26}$H$_{24}$N$_3$O$_2$Cl Calcd.: C, 70.03; H, 5.42; N, 9.42 Found: C, 69.77; H, 5.39; N, 9.25

Example 41

N-(4-Chlorobenzyl)-N'-(1,2-dihydro-2,6,7-trimethyl-1-oxo-4-phenylisoquinolin-3-yl)urea Melting point: 208°–210.5° C. (recrystallized from tetrahydrofuran-isopropyl ether)

NMR (200 MHz, CDCl$_3$) ppm: 2.13 (3H, s), 2.16 (3H, s), 3.47 (3H, s), 4.19 (2H, d, J=5.0 Hz), 6.15 (1H, m), 6.69 (1H, s), 6.77 (1H, s), 6.85–7.00 (1H, m), 7.05–7.20 (5H, m), 7.25–7.40 (3H, m), 7.81 (1H, s)

Elemental analysis for C$_{26}$H$_{24}$N$_3$O$_2$Cl Calcd.: C, 70.03; H, 5.42; N, 9.42 Found: C, 69.91; H, 5.38; N, 9.32

Example 42

N-(2-Chlorobenzyl)-N'-(1,2-dihydro-2,6,7-trimethyl-1-oxo-4-phenylisoquinolin-3-yl)urea Melting point: about 230° C. (decomp.) (recrystallized from tetrahydrofuran-isopropyl ether)

NMR (200 MHz, CDCl$_3$) ppm: 2.22 (3H, s), 2.34 (3H, s), 3.59 (3H, s), 4.38 (2H, bs), 6.20 (1H, bm), 6.88 (1H, s), 7.10–7.45 (10H, m), 8.15 (1H, s)

Elemental analysis for C$_{26}$H$_{24}$N$_3$O$_2$Cl Calcd.: C, 70.03; H, 5.42; N, 9.42 Found: C, 69.73; H, 5.34; N, 9.13

Example 43

N-Carbobenzyloxymetyl-N'-(1,2-dihydro-2,6,7-trimethyl-1-oxo-4-phenylisoquinolin-3-yl)urea Melting point: 200.5°–201° C. (recrystallized from tetrahydrofuran-isopropyl ether )

NMR (200 MHz, CDCl$_3$) ppm: 2.17 (3H, s), 2.26 (3H, s), 3.57 (3H, s), 4.00 (2H, d, J=5.6 Hz), 5.14 (2H, s), 5.96 (1H, m), 6.48 (1H, s), 6.84 (1H, s), 7.20–7.50 (10H, m), 8.01 (1H, s)

Elemental analysis for C$_{28}$H$_{27}$N$_3$O$_4$.0.1H$_2$O Calcd.: C, 71.35; H, 5.82; N, 8.92 Found: C, 71.13; H, 5.85; N, 9.03

Example 44

N-(2-Chlorobenzyl)-N'-[4-(2-ethylphenyl)-1,2-dihydro-2-methyl-1-oxoisoquinolin-3-yl)-N-methylurea Melting point: 158°–161° C. (recrystallized for ethyl acetate)

NMR (200 MHz, CDCl$_3$) ppm: 0.94 (3H, t, J=7.6 Hz), 2.34 (2H, m), 2.70 (3H, s), 3.67 (3H, s), 4.58 (2H, s), 5.71 (1H, bs, NH), 6.83 (1H, dd, J=7.2, 2.0 Hz), 6.93 (1H, dd, J=7.0, 2.2 Hz), 7.17–7.52 (9H, m), 8.48 (1H, dd, J=7.0, 2.6 Hz)

Elemental analysis for C$_{27}$H$_{26}$N$_3$O$_2$Cl Calcd.: C, 70.50; H, 5.70; N, 9.14 Found: C, 70.11; H, 5.78; N, 8.83

Example 45

N-[2-Carbo(1,1-dimethylethyl)oxyethyl]-N'-(1,2-dihydro-2,6,7-trimethyl-1-oxo-4-phenylisoquinolin-3yl)urea Melting point: 175°–176° C. (recrystallized from tetrahydrofuran-isopropyl ether)

NMR (200 MHz, CDCl$_3$) ppm: 1.40 (9H, s), 2.22 (3H, s), 2.35 (3H, s), 2.35 (2H, t), 3.30–3.40 (2H, m), 3.58 (3H, s), 5.39 (1H, m), 6.24 (1H, s), 6.88 (1H, s), 7.20–7.30 (2H, m), 7.35–7.50 (3H, m), 8.17 (1H, s)

Elemental analysis for C$_{26}$H$_{31}$N$_3$O$_4$ Calcd.: C, 69.47; H, 6.95; N, 9.35 Found: C, 69.44; H, 6.96 N, 9.47

Example 46

N-(2-Bromobenzyl)-N'-(1,2-dihydro-2,6,7-trimethyl-1-oxo-4-phenylisoquinolin-3-yl)urea Melting point: 239°–241° C. (recrystallized from tetrahydrofuran-isopropyl ether)

NMR (200 MHz, CDCl$_3$) ppm: 2.23 (3H, s), 2.36 (3H, s), 3.62 (3H, s), 4.39 (2H, bs), 6.34 (1H, m), 6.90 (1H, s), 7.10–7.60 (10H, m), 8.18 (1H, s)

Elemental analysis for C$_{26}$H$_{24}$N$_3$O$_2$Br.0.2H$_2$O Calcd.: C, 63.22; H, 4.98; N, 8.51 Found: C, 63.11; H, 4.95; N, 8.53

Example 47

N-(2,6-Dichlorobenzyl)-N'-(1,2-dihydro-2,6,7-trimethyl-1-oxo-4-phenylisoquinolin-3-yl)urea Melting point: about 237° C. (decomp.) (recrystallized from tetrahydrofuran-isopropyl ether)

NMR (200 MHz, CDCl$_3$) ppm: 2.23 (3H, s), 2.36 (3H, s), 3.61 (3H, s), 4.65 (2H, bs), 6.18 (1H, m), 6.91 (1H, s), 7.15–7.45 (9H, m), 8.17 (1H, s)

Elemental analysis for C$_{26}$H$_{23}$N$_3$O$_2$Cl$_2$ Calcd.: C, 65.01; H, 4.83; N, 8.75 Found: C, 64.68; H, 4.91; N, 8.43

Example 48

N-(1,2-Dihydro-2,6,7-trimethyl-1-oxo-4-phenylisoquinolin-3-yl)-N'-(2-nitrobenzyl)urea Melting point: 216°–216.5° C. (recrystallized from tetrahydrofuran-isopropyl ether)

NMR (200 MHz, CDCl$_3$) ppm: 2.22 (3H, s), 2.35 (3H, s), 3.58 (3H, s), 4.58 (2H, d, J=6.6 Hz), 6.57 (1H, m), 6.88 (1H, s), 7.10–7.70 (9H, m), 8.06 (1H, dd, J=8.2, 1.2 Hz), 8.17 (1H, s)

Elemental analysis for C$_{26}$H$_{24}$N$_4$O$_4$ Calcd.: C, 68.41; H, 5.30; N, 12.27 Found: C, 68.34; H, 5.45; N, 12.18

Example 49

N-Cyclohexylmethyl-N'-[4-(2-ethylphenyl)-1,2-dihydro-2,6,7-trimethyl-1-oxoisoquinolin-3-yl)-N-methyl)urea A colorless oil NMR (200 MHz, CDCl$_3$) ppm: 1.13 (3H, t, J=7.6 Hz), 1.40–1.80 (9H, m), 2.23 (3H, s), 2.32 (2H, m), 2.39 (3H, s), 2.89 (3H, s), 3.45 (3H, s), 3.86 (2H, bs), 6.70 (1H, s), 7.10–3.34 (4H, m), 8.26 (1H, s)

Example 50

N-(2,4-Dichlorobenzyl)-N'-(1,2-dihydro-2,6,7-trimethyl-1-oxo-4-phenylisoquinolin-3-yl)urea Melting point: 212.5°–214° C. (recrystallized from tetrahydrofuran-isopropyl ether)

NMR (200 MHz, CDCl$_3$) ppm: 2.22 (3H, s), 2.34 (3H, s), 3.58 (3H, s), 4.32 (2H, bs), 6.31 (1H, m), 6.88 (1H, s), 7.05–7.45 (9H, m), 8.14 (1H, s)

Elemental analysis for C$_{26}$H$_{23}$N$_3$O$_2$Cl$_2$ Calcd.: C, 65.01; H, 4.83; N, 8.75 Found: C, 65.01; H, 4.96; N, 8.72

Example 51

N-(1,2-Dichloro-2,6,7-trimethyl-1-oxo-4-phenylisoquinolin-3-yl)-N'-[4-(dimethylamino)benzyl]urea Melting point: 215°–215.5° C. (recrystallized from tetrahydrofuran-isopropyl ether)

NMR (200 MHz, CDCl$_3$) ppm: 2.20 (3H, s), 2.30 (3H, s), 2.92 (6H, s), 3.54 (3H, s), 4.16 (2H, d, J=5.4 Hz), 5.17 (1H, t, J=5.4 Hz), 6.12 (1H, s), 6.64 (1H, d, J=8.8 Hz), 6.85 (1H, s), 7.04 (1H, d, J=8.8 Hz), 7.18 (2H, m), 7.37 (3H, m), 8.09 (1H, s)

Elemental analysis for C$_{28}$H$_{30}$N$_4$O$_2$ Calcd.: C, 73.98; H, 6.65; N, 12.33 Found: C, 73.80; H, 6.54; N, 12.49

Example 52

N-(2-Chlorobenzyl)-N'-(1,2-dihydro-2,6,7-trimethyl-1-oxo-4-phenylisoquinolin-3-yl)-N-methyl]urea Melting point: about 207° C. (decomp.) (recrystallized from tetrahydrofuran-isopropyl ether)

NMR (200 MHz, CDCl$_3$) ppm: 2.23 (3H, s), 2.36 (3H, s), 2.72 (3H, s), 3.62 (3H, s), 4.49 (2H, s), 5.81 (1H, s), 6.84 (1H, s), 6.94 (1H, m), 7.15–7.50 (8H, m), 8.21 (1H, s)

Elemental analysis for C$_{27}$H$_{26}$N$_3$O$_2$Cl Calcd.: C, 70.50; H, 5.70; N, 9.14 Found: C, 70.69; H, 5.80; N, 8.98

Example 53

N-Benzyl-N-ethyl-N'-(1,2-dihydro-2,6,7-trimethyl-1-oxo-4-phenylisoquinolin-3-yl)urea Melting point: 153°–155° C. (recrystallized from tetrahydrofuran-isopropyl ether)

NMR (200 MHz, CDCl$_3$) ppm: 0.88 (3H, t, J=7.1 Hz), 2.23 (3H, s), 2.36 (3H, s), 3.14 (2H, m), 3.61 (3H, s), 4.32 (2, s), 5.69 (1H, s), 6.84 (1H, s), 7.00–7.10 (2H, m), 7.26 (5H, m), 7.42 (3H, m), 8.22 (1H, s)

Elemental analysis for C$_{28}$H$_{29}$N$_3$O$_2$.0.4H$_2$O Calcd.: C, 75.28; H, 6.28; N, 9.41 Found: C, 75.18; H, 6.79; N, 9.15

Example 54

N-Benzyl-N'-(1,2-dihydro-2,6,7-trimethyl-1-oxo-4-phenylisoquinolin-3-yl)-N-(1-methylethyl)urea Melting point: 161°–164° C. (recrystallized from tetrahydrofuran-isopropyl ether)

NMR (200 MHz, CDCl$_3$) ppm: 1.06 (6H, d, J=6.6 Hz), 2.21 (3H, s), 2.35 (3H, s), 3.53 (3H, s), 3.89 (1H, m), 4.18 (1H, m), 4.47 (1H, m), 5.53 (1H, s), 6.80 (1H, s), 6.98 (2H, m), 7.15–7.35 (5H, m), 7.46 (3H, m), 8.19 (1H, s)

Elemental analysis for C$_{29}$H$_{31}$N$_3$O$_2$ Calcd.: C, 76.79; H, 6.89; N, 9.26 Found: C, 76.39; H, 6.88; N, 9.40

Example 55

N,N-Dibenzyl-N'-(1,2-dihydro-2,6,7-trimethyl-1-oxo-4-phenylisoquinolin-3-yl)urea Melting point: 192°–193.5° C. (recrystallized from tetrahydrofuran-isopropyl ether)

NMR (200 MHz, CDCl$_3$) ppm: 2.22 (3H, s), 2.35 (3H, s), 3.56 (3H, s), 4.31 (4H, bs), 5.76 (1H, s), 6.81 (1H, s), 7.04 (4H, m), 7.20–7.55 (11H, m), 8.20 (1H, s)

Elemental analysis for C$_{33}$H$_{31}$N$_3$O$_2$.0.2H$_2$O Calcd.: C, 78.45; H, 6.26; N, 8.32 Found: C, 78.49; H, 6.46; N, 8.60

Example 56

N-Benzyl-N'-(1,2-dihydro-2,6,7-trimethyl-1-oxo-4-(2-methylphenyl)-1-oxoisoquinolin-3-yl]-N-methylurea Melting point: 170°–174° C. (decomp.) (recrystallized from ethyl acetate)

NMR (200 MHz, CDCl$_3$) ppm: 2.02 (3H, s), 2.22 (3H, s), 2.37 (3H, s), 2.61 (3H, s), 3.66 (3H, s), 4.34 (2H, bs), 5.66 (1H, bs, NH), 6.66 (1H, s), 6.98 (2H, m), 7.12–7.39 (7H, m), 8.24 (1H, s)

Elemental analysis for C$_{28}$H$_{29}$N$_3$O$_2$.0.2H$_2$O Calcd.: C, 75.89; H, 6.69; N, 9.48 Found: C, 75.89; H, 6.57; N, 9.32

Example 57

N-Benzyl-N'-[1,2-dihydro-2,6,7-trimethyl-1-oxo-4-(2-methylphenyl)-1-oxoisoquinolin-3-yl]urea Melting point: 198°–200.5° C. (recrystallized from ethyl acetate)

NMR (200 MHz, CDCl$_3$) ppm: 1.97 (3H, s), 2.21 (3H, s), 2.35 (3H, s), 3.62 (3H, s), 4.30 (2H, bt, J=5.8 Hz), 4.94 (1H, bt, J=4.4 Hz, NH), 5.79 (1H, s, NH), 6.65 (1H, s), 7.03–7.36 (9H, m), 8.18 (1H, s)

Elemental analysis for C$_{27}$H$_{27}$N$_3$O$_2$ Calcd.: C, 76.21; H, 6.40; N, 9.87 Found: C, 75.87; H, 6.62; N, 9.73

Example 58

N-(2-Chlorobenzyl)-N'-[1,2-dihydro-2,6,7-trimethyl-4-(2-methylphenyl)-1-oxoisoquinolin-3-yl]urea Melting point: 219°–221° C. (recrystallized from ethyl acetate)

NMR (200 MHz, CDCl$_3$) ppm: 1.92 (3H, s), 2.20 (3H, s), 2.32 (3H, s), 3.56 (3H, s), 4.36 (2H, d, J=5.6 Hz), 5.50 (1H, bt, NH), 6.39 (1H, s, NH), 6.65 (1H, s), 7.02–7.32 (8H, m), 8.10 (1H, s)

Elemental analysis for C$_{27}$H$_{26}$N$_3$O$_2$Cl.0.1H$_2$O Calcd.: C, 70.22; H, 5.72; N, 9.10 Found: C, 70.08; H, 5.80; N, 8.80

Example 59

N-Benzyl-N'-[4-(2-ethylphenyl)-1,2-dihydro-2,6,7-trimethyl-1-oxoisoquinolin-3-yl]-N-methylurea Melting point: 180°–182° C. (recrystallized from ethyl acetate)

NMR (200 MHz, CDCl$_3$) ppm: 0.96 (3H, t, J=7.6 Hz), 2.21 (3H, s), 2.32 (2H, m), 2.36 (3H, s), 2.61 (3H, s), 3.65 (3H, s), 4.33 (2H, bs), 5.67 (1H, bs, NH), 6.66 (1H, s), 6.96 (2H, bt, J=3.6 Hz ), 7.12–7.41 (7H, m), 8.22 (1H, s)

Elemental analysis for C$_{29}$H$_{31}$N$_3$O$_2$ Calcd.: C, 76.79; H, 6.89; N, 9.26 Found: C, 76.43; H, 6.92; N, 9.39

Example 60

N-(2-Chlorobenzyl)-N'-[4-(2-ethylphenyl)-1,2-dihydro-2,6,7-trimethyl-1-oxoisoquinolin-3-yl]urea Melting point: 204°–207° C. (recrystallized from ethyl acetate)

NMR (200 MHz, CDCl$_3$) ppm: 0.95 (3H, t, J=7.4 Hz), 2.21 (3H, s), 2.28 (2H, m), 2.36 (3H, s), 3.61 (3H, s), 4.39 (1H, bd, J=4.0 Hz), 5.07 (1H, bt, NH), 5.75 (1H, s, NH) 6.6 (1H, s), 7.01 (1H, d, J=7.0 Hz) 7.12–7.38 (7H, m), 8.20 (1H, s)

Elemental analysis for C$_{28}$H$_{28}$N$_3$O$_2$Cl.0.2H$_2$O Calcd.: C, 70.42; H, 5.99; N, 8.80 Found: C, 70.15; H, 5.77 N, 8.72

Example 61

N-Benzyl-N'-[1,2-dihydro-2,6,7-trimethyl-4-(2,6-dimethylphenyl)-1-oxoisoquinolin-3-yl]-N-methylurea Melting point: 212°–214° C. (recrystallized from ethyl acetate)

NMR (200 MHz, CDCl$_3$) ppm: 1.97 (6H, s), 2.22 (3H, s), 2.38 (3H, s), 2.60 (3H, s), 3.67 (3H, s), 4.32(2H, bs), 5.53 (1H, s, NH) 6.61 (1H, s), 6.94–6.99 (2H, m), 7.12–7.31 (6H, m), 8.26 (1H, s)

Elemental analysis for C$_{29}$H$_{31}$N$_3$O$_2$.0.3H$_2$O Calcd.: C, 75.89; H, 6.93; N, 9.15 Found: C, 75.75; H, 6.85 N, 9.22

Example 62

N-(2-Chlorobenzyl)-N'-[1,2-dihydro-2,6,7-trimethyl-4-(2,6-dimethylphenyl)-1-oxoisoquinolin-3-yl]urea Melting point: 258°–261.5° C. (recrystallized from ethyl acetate-methanol)

NMR (200 MHz, CDCl$_3$) ppm: 1.89 (6H, s), 2.21 (3H, s), 2.37 (3H, s), 3.63 (3H, s), 4.38 (2H, d, J=5.8 Hz), 5.11 (1H, bs, NH), 5.61 (1H, s, NH), 6.59 (1H, s), 7.08–7.36 (7H, m), 8.22 (1H, s)

Elemental analysis for C$_{28}$H$_{28}$N$_3$O$_2$.0.2H$_2$O Calcd.: C, 70.42; H, 5.99; N, 8.80 Found: C, 70.29; H, 6.05 N, 8.48

Example 63

N-Benzyl-N'-[1,2-dihydro-2-methyl-4-(2-methylphenyl)-1-oxoisoquinolin-3-yl]-N-methylurea Melting point: 166°–168° C. (recrystallized from ethyl acetate)

NMR (200 MHz, CDCl$_3$) ppm: 2.02 (3H, s), 2.63 (3H, s), 3.68 (3H, s), 4.35 (2H, bs), 5.71 (1H, bs, NH), 6.89–7.00 (3H, m), 7.17–7.50 (9H, m), 8.49 (1H, dd, J=7.0, 2.4 Hz)

Elemental analysis for C$_{26}$H$_{25}$N$_3$O$_2$.0.2H$_2$O Calcd.: C, 75.23; H, 6.17; N, 10.12 Found: C, 75.33; H, 6.04 N, 10.18

Example 64

N-(2-Chlorobenzyl)-N'-[1,2-dihydro-2-methyl-4-(2-methylphenyl)-1-oxoisoquinolin-3-yl]urea Melting point: 208.5°–210.5° C. (recrystallized from ethyl acetate)

NMR (200 MHz, CDCl$_3$) ppm: 1.93 (3H, s), 3.60 (3H, s), 4.38 (2H, d, J=5.8 Hz), 5.28 (1H, bt, J=5.8 Hz, NH), 6.12 (1H, s, NH), 6.91 (1H, dd, J=7.2, 1.6 Hz), 7.03–7.49 (10H, m), 8.39 (1H, dd, J=7.4, 1.6 Hz)

Elemental analysis for C$_{25}$H$_{22}$N$_3$O$_2$Cl Calcd.: C, 69.52; H, 5.13; N, 9.73 Found: C, 69.71; H, 5.06 N, 9.98

Example 65

N-Benzyl-N'-[4-(2-ethylphenyl)-1,2-dihydro-2-methyl-1-oxoisoquinolin-3-yl]-N-methylurea Melting point: 179°–180° C. (recrystallized from ethyl acetate)

NMR (200 MHz, CDCl$_3$) ppm: 0.95 (3H, t, J=7.4 Hz), 2.34 (2H, m), 2.63 (3H, s), 3.68 (3H, s), 5.68 (1H, bs, NH) 6.90–7.48 (12H, m), 8.48 (1H, dd, J=7.2, 2.2 Hz)

Elemental analysis for C$_{27}$H$_{27}$N$_3$O$_2$.0.2H$_2$O Calcd.: C, 75.57; H, 6.44; N, 9.79 Found: C, 75.63; H, 6.44; N, 10.03

Example 66

N-(2-Chlorobenzyl)-N'-[4-(2-ethylphenyl)-1,2-dihydro-2-methyl-1-oxoisoquinolin-3-yl]urea Melting point: 189.5°–191.5° C. (recrystallized from ethyl acetate)

NMR (200 MHz, CDCl$_3$) ppm: 0.93 (3H, t, J=7.6 Hz), 2.27 (2H, m), 3.61 (3H, s), 4.39 (2H, d, J=6.2 Hz), 5.21 (1H, b, J=6.2 Hz, NH), 5.93 (1H, s, NH), 6.93 (1H, dd, J=7.2, 2.4 Hz), 7.03 (1H, d, J=7.2 Hz), 7.11–7.45 (9H, m), 8.39 (1H, dd, J=7.2, 2.2 Hz)

Elemental analysis for C$_{26}$H$_{24}$N$_3$O$_2$Cl Calcd.: C, 70.03; H, 5.42; N, 9.42 Found: C, 70.00; H, 5.58; N, 9.53

Example 67

N-Benzyl-N'-[1,2-dihydro-2-methyl-4-(2,6-dimethylphenyl)-1-oxoisoquinolin-3-yl]-N-methylurea Melting point: 200°–202.5° C. (recrystallized from ethyl acetate-methanol)

NMR (200 MHz, CDCl$_3$) ppm: 1.97 (6H, s), 2.62 (3H, s), 3.69 (3H, s), 4.34 (2H, bs), 5.58 (1H, s, NH), 6.88 (1H, dd, J=6.6, 2.4 Hz), 6.94–7.49 (10H, m), 8.51 (1H, dd, J=6.4, 2.4 Hz)

Elemental analysis for C$_{27}$H$_{27}$N$_3$O$_2$ Calcd.: C, 76.21; H, 6.40; N, 9.87 Found: C, 76.13; H, 6.54; N, 10.07

Example 68

N-(2-Chlorobenzyl)-N'-[1,2-dihydro-2-methyl-4-(2,6-dimethylphenyl)-1-oxoisoquinolin-3-yl]urea Melting point: 185°–187.5° C. (recrystallized from ethyl acetate)

NMR (200 MHz, CDCl$_3$) ppm: 1.88 (6H, s), 3.61 (3H, s), 4.38 (2H, d, J=6.0 Hz), 5.55 (1H, bt, J=26 Hz,NH), 6.20 (1H, s, NH), 6.84 (1H, d, J=7.6 Hz), 7.04–7.47 (9H, m), 8.36 (1H, dd, J=7.2, 1.8 Hz)

Elemental analysis for C$_{26}$H$_{24}$N$_3$O$_2$Cl.0.2H$_2$O Calcd.: C, 69.46; H, 5.86; N, 9.34 Found: C, 69.17; H, 5.60; N, 9.24

Example 69

N-Benzyl-N'-[4-(4-fluoro-2-methylphenyl)-1,2-dihydro-2-methyl-1-oxoisoquinolin-3-yl]-N-methylurea Melting point: 100°–102° C. (recrystallized from ethyl acetate)

NMR (200 MHz, CDCl₃) ppm: 1.96 (3H, s), 2.76 (3H, s), 3.65 (3H, s), 4.39 (2H, bs), 5.68 (1H, bs, NH), 6.87 (1H, dd, J=7.0, 2.4 Hz), 6.92–7.52 (10H, m), 8.47(1H, dd, J=7.2, 2.4 Hz)

Elemental analysis for $C_{26}H_{24}N_3O_2F.0.3\ H_2O$ Calcd.: C, 71.81; H, 5.70; N, 9.66 Found: C, 71.76; H, 5.70; N, 9.60

Example 70

N-(2-Chlorobenzyl)-N'-[4-(4-fluoro-2-methylphenyl)-1,2-dihydro-2-methyl-1-oxoisoquinolin-3-yl]urea Melting point: 220.5°–222° C. (recrystallized from ethyl acetate)

NMR (200 MHz, CDCl₃) ppm: 1.91 (3H, s), 3.61 (3H, s), 4.40 (2H, d, J=6.6 Hz 5.32 (1H, bt, J=6.6 Hz, NH) 6.11 (1H, s, NH), 6.75–7.55 (10H, m), 8.40 (1H, dd, J=7.9, 0.9 Hz)

Elemental analysis for $C_{25}H_{21}N_3O_2ClF$ Calcd.: C, 66.74; H, 4.70; N, 9.34 Found: C, 66.44; H, 4.81; N, 9.16

Example 71

N-Benzyl-N'-(6-chloro-1,2-dihydro-2-methyl-1-oxo-4-phenylisoquinolin-3-yl)-N-methylurea Melting point: 123°–125° C. (decomp.) (recrystallized from ethyl acetate-methanol)

NMR (200 MHz, CDCl₃) ppm: 2.67 (3H, s), 3.64 (3H, s), 4.39 (2H, brs), 5.73 (1H, s, NH), 7.04 (2H, m), 7.22–7.44 (10H, m), 8.40 (1H, d, J=8.6 Hz)

Elemental analysis for $C_{25}H_{22}N_3O_2Cl.0.5H_2O$ Calcd.: C, 68.10; H, 5.26; N, 9.53 Found: C, 68.25; H, 4.97; N, 9.83

Example 72

N-(1,2-Dihydro-2,6,7-trimethyl-1-oxo-4-phenylisoquinolin-3-yl)-N'-(3,5-dimethylbenzyl)urea Melting point: about 230° C. (decomp.) (recrystallized from tetrahydrofuran-isopropyl ether)

NMR (200 MHz, CDCl₃) ppm: 2.22 (3H, s), 2.29 (6H, s), 2.33 (3H, s), 3.60 (3H, s), 4.24 (2H, bd, J=4.8 Hz), 5.96 (1H, m), 6.81 (2H, s), 6.88 (2H, s), 6.95 (1H, s), 7.20–7.45 (5H, m), 8.14 (1H, s)

Elemental analysis for $C_{28}H_{29}N_3O_2.0.2H_2O$ Calcd.: C, 75.89; H, 6.69; N, 9.48 Found: C, 76.01; H, 6.79; N, 9.31

Example 73

N-(1,2-Dihydro-2,6,7-trimethyl-1-oxo-4-phenylisoquinolin-3-yl)-N'-(3,5-dimethylbenzyl)-N'-methylurea Melting point: 184°–185° C. (recrystallized from ethyl acetate-isopropyl ether)

NMR (200 MHz, CDCl₃) ppm: 2.23 (3H, s), 2.30 (6H, s), 2.37 (3H, s), 2.65 (3H, s), 3.64 (3H, s), 4.29 (2H, bs), 5.71 (1H, s), 6.74 (2H, s), 6.86 (1H, s), 6.92 (1H, s), 7.20–7.45 (5H, m), 8.23 (1H, s)

Elemental analysis for $C_{29}H_3N_3O_2.0.1H_2O$ Calcd.: C, 76.49; H, 6.91; N, 9.23 Found: C, 76.30; H, 6.93; N, 9.30

Example 74

N-[3,5-Bis(trifluoromethyl)benzyl]-N'-(1,2-dihydro-2,6,7-trimethyl-1-oxo-4-phenylisoquinolin-3-yl)urea Melting point: about 230° C. (decomp.) (recrystallized from tetrahydrofuran-isopropyl ether)

NMR (200 MHz, CDCl₃) ppm: 2.23 (3H, s), 2.35 (3H, s), 3.63 (3H, s), 4.45 (2H, bs), 6.58 (1H, m), 6.89 (1H, s), 7.15–7.50 (6H, m), 7.71 (2H, s), 7.78 (1H, s), 8.17 (1H, s)

Elemental analysis for $C_{28}H_{23}N_3O_2F_6$ Calcd.: C, 64.43; H, 4.23; N, 7.67 Found: C, 61.47; H, 4.54; N, 7.84

Example 75

N-(2-Aminobenzyl)-N'-(1,2-dihydro-2,6,7-trimethyl-1-oxo-4-phenylisoquinolin-3-yl)urea Using the compound obtained in Example 48, in a mixed solvent of tetrahydrofuran and ethanol, catalytic hydrogenation using palladium-carbon as a catalyst was carried out to provide the title compound as colorless crystals.

Melting point: 217.5°–218.3° C. (recrystallized from tetrahydrofuran-isopropylether)

NMR (200 MHz, CDCl₃) ppm: 2.23 (3H, s), 2.37 (3H, s), 3.61 (3H, s), 4.24 (2H, m), 4.42 (2H, bs), 6.34 (1H, m), 6.55–6.75 (2H, m), 6.85–7.15 (3H, m), 7.20–7.45 (6H, m), 8.17 (1H, s)

Elemental analysis for $C_{26}H_{26}N_4O_2.0.2H_2O$ Calcd.: C, 72.60; H, 6.19; N, 13.03 Found: C, 72.71; H, 6.22; N, 12.85

FORMULATION EXAMPLE

Tablets

Of the components given below, to the compound of Example 1, corn starch and lactose were added with aqueous hydroxypropylcellulose, and the mixture was kneaded, then dried and crushed to give granules.

To this was added magnesium stearate and, after admixing, the whole mixture was made up into tablets each weighing 200 mg on a rotary tableting machine.

| | |
|---|---|
| Compound of Example 1 | 50 mg |
| Lactose | 100 mg |
| Corn starch | 43.4 mg |
| Hydroxypropylcellulose | 6 mg |
| Magnesium stearate | 0.6 mg |
| Total | 200 mg |

What is claimed is:

1. A tachykinin receptor antagonist composition characterized by comprising a compound of the formula:

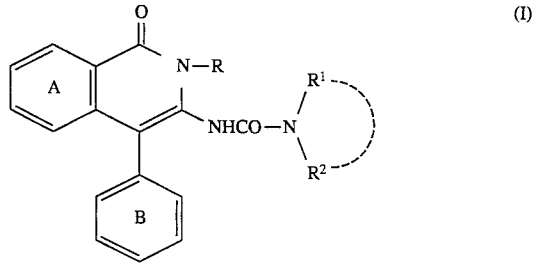

(I)

wherein ring A and ring B each means a benzene ring, wherein ring A may be substituted with 1 to 4 $C_{1-6}$ alkyl groups which may be the same or different and wherein ring B may be substituted with 1 to 4 $C_{1-6}$ alkyl groups or $C_{1-6}$ alkoxy groups which may be the same or different; R means a $C_{1-6}$ alkyl; $R^1$ is methyl, which may be substituted with furyl, thienyl, pyridyl, cyclohexyl, or phenyl, wherein the phenyl ring may be substituted with alkyl, alkoxy or halogen; $R^2$ is hydrogen or alkyl or a pharmaceutically acceptable salt thereof; and a pharmaceutically acceptable carrier.

2. A composition as claimed in claim 1, wherein the moiety

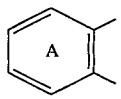

of formula (I) is

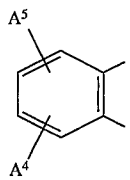

wherein $A^4$ and $A^5$ each is a $C_{1-4}$ alkyl group.

3. A composition as claimed in claim 2, wherein $A^4$ and $A^5$ respectively are methyl.

4. The antagonist composition as claimed in claim 1, wherein the tachykinin receptor is substance P receptor.

5. A compound of the formula:

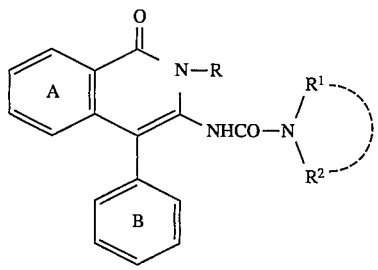

wherein ring A and ring B each means a benzene ring, wherein ring A may be substituted with 1 to 4 $C_{1-6}$ alkyl groups which may be the same or different and wherein ring B may be substituted with 1 to 4 $C_{1-6}$ alkyl groups or $C_{1-6}$ alkoxy groups which may be the same or different; R means a $C_{1-6}$ alkyl; $R^1$ is methyl, which may be substituted with furyl, thienyl, pyridyl, cyclohexyl, or phenyl, wherein the phenyl ring may be substituted with alkyl, alkoxy or halogen; $R^2$ is hydrogen or alkyl; or a salt thereof.

6. A compound as claimed in claim 5, wherein the ring A is a group of the formula:

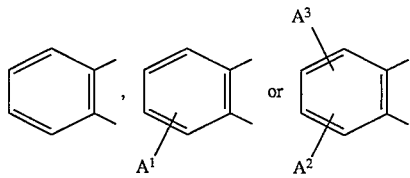

wherein $A^1$, $A^2$ and $A^3$ independently means, a $C_{1-4}$ alkyl.

7. A compound as claimed in claim 5, wherein the ring A is a group of the formula:

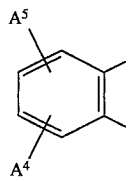

wherein $R^4$ and $R^5$ independently means a $C_{1-4}$ alkyl group.

8. A compound as claimed in claim 5, wherein the ring B is a group of the formula:

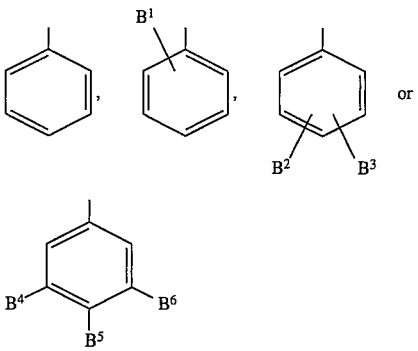

wherein $B^1$, $B^2$, $B^3$, $B^4$, $B^5$ and $B^6$ independently means, a $C_{1-4}$ alkyl or a $C_{1-4}$ alkoxy.

9. A compound as claimed in claim 5, wherein the ring B is a group of the formula:

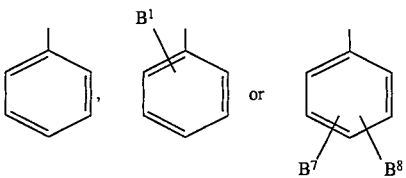

wherein $B^1$ means, a $C_{1-4}$ alkyl or a $C_{1-4}$ alkoxy, and $B^7$ and $B^8$ independently means a $C_{1-4}$ alkyl group.

10. A compound as claimed in claim 5, wherein R is a $C_{1-4}$ alkyl.

11. A compound as claimed in claim 5, wherein ring A and B each is a benzene ring, wherein ring A may be substituted with 1 to 4 $C_{1-6}$ alkyl groups which may be the same or different and ring B may be substituted with 1 to 4 $C_{1-6}$ alkyl groups or $C_{1-6}$ alkoxy groups which may be the same or different; R is a $C_{1-4}$ alkyl; $R^1$ is methyl, which may be substituted with furyl, thienyl, pyridyl, cyclohexyl, or phenyl, wherein the phenyl ring may be substituted with alkyl, alkoxy or halogen; $R^2$ is hydrogen or alkyl.

12. A compound as claimed in claim 5, which is N-benzyl-N'-[1,2-dihydro-2,6,7-trimethyl-1-oxo-4-phenylisoquinoline-3-yl]-N-methylurea.

13. A compound as claimed in claim 5, which is N-[1,2-dihydro-2,6,7-trimethyl-1-oxo-4-phenylisoquinoline-3-yl]-N'-(2-methoxybenzyl)-N'-methylurea.

14. A compound as claimed in claim 5, which is N-(2-chlorobenzyl)-N'-[1,2-dihydro-2,6,7-trimethyl-1-oxo-4-phenylisoquinoline-3-yl]-N-methylurea.

15. A compound as claimed in claim 5, which is N-benzyl-N-ethyl-N'-[1,2-dihydro-2,6,7-trimethyl-1-oxo-4-phenyl-isoquinoline-3-yl]urea.

16. Method for treating pain in mammals which comprises administering to a subject suffer therefrom an effective amount of a compound ($I^a$) as claimed in claim 5 or a pharmaceutically acceptable salt with a physiologically acceptable carrier.

17. Method for antagonizing a tachykinin receptor in mammals which comprises administering to a subject in need an effective amount of a composition as claimed in claim 1.

* * * * *